(12) United States Patent
Birnbach et al.

(10) Patent No.: US 11,471,848 B1
(45) Date of Patent: Oct. 18, 2022

(54) UNIVERSAL CHEMICAL PROCESSOR

(71) Applicant: Advanced Fusion Systems LLC, Newtown, CT (US)

(72) Inventors: Curtis Birnbach, New Rochelle, NY (US); William Joyce, Newtown, CT (US)

(73) Assignee: ADVANCED FUSION SYSTEMS LLC, Newtown, CT (US)

( * ) Notice: Subject to any disclaimer, the term of this patent is extended or adjusted under 35 U.S.C. 154(b) by 0 days.

(21) Appl. No.: 17/508,469

(22) Filed: Oct. 22, 2021

(51) Int. Cl.
| | |
|---|---|
| *B01J 8/42* | (2006.01) |
| *A61L 2/26* | (2006.01) |
| *B01J 8/00* | (2006.01) |
| *B01J 19/12* | (2006.01) |
| *B01J 19/26* | (2006.01) |
| *C01B 7/19* | (2006.01) |
| *C01B 25/223* | (2006.01) |
| *C01F 11/46* | (2006.01) |
| *C01B 15/027* | (2006.01) |
| *C02F 1/30* | (2006.01) |
| *B63H 21/12* | (2006.01) |
| *B63H 11/02* | (2006.01) |

(Continued)

(52) U.S. Cl.
CPC ............ *B01J 8/42* (2013.01); *A61L 2/082* (2013.01); *A61L 2/26* (2013.01); *B01J 8/004* (2013.01); *B01J 19/125* (2013.01); *B01J 19/26* (2013.01); *B63B 35/32* (2013.01); *B63H 11/02* (2013.01); *B63H 21/12* (2013.01); *C01B 7/191* (2013.01); *C01B 15/027* (2013.01); *C01B 25/223* (2013.01); *C01F 11/46* (2013.01); *C02F 1/307* (2013.01); *A61L 2202/11* (2013.01); *A61L 2202/16* (2013.01); *C02F 2101/32* (2013.01); *C02F 2103/007* (2013.01); *C02F 2103/08* (2013.01); *C02F 2201/008* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 6,228,266 B1 * | 5/2001 | Shim ............... | C02F 1/4608 |
| | | | 210/243 |
| 9,406,478 B2 * | 8/2016 | Birnbach .......... | C01D 3/04 |

(Continued)

*Primary Examiner* — Chester T Barry
(74) *Attorney, Agent, or Firm* — Leason Ellis LLP

(57) ABSTRACT

A universal chemical processor (UCP) including a reactor vessel with a main chamber, comprises inlets for feedstock, a fluidizing medium and reactants. The UCP further includes a reactive X-ray chemical processor (RXCP) having a large area hollow cylindrical cold cathode in the main chamber, a grid positioned concentrically with respect to the cathode, and an anode positioned concentrically with respect to the cathode and grid. In operation, when activated, the cathode of the RXCP emits electrodes onto the anode, which then emits X-rays into a radiation zone within the main chamber capable of ionizing feedstock and reactants, inducing chemical reactions, and sterilizing and decomposing organic materials within the radiation zone, and wherein, a fluidized bed is supported in the main chamber when the fluidizing medium and feedstock are supplied. The RXCP and the fluidized bed portions can be operated separately or in conjunction to achieve unanticipated results.

23 Claims, 10 Drawing Sheets

(51) Int. Cl.
*B63B 35/32* (2006.01)
*A61L 2/08* (2006.01)
C02F 101/32 (2006.01)
C02F 103/00 (2006.01)
C02F 103/08 (2006.01)

(56) References Cited

U.S. PATENT DOCUMENTS

| | | | | |
|---|---|---|---|---|
| 2003/0129385 A1* | 7/2003 | Hojo | ................... | B29D 17/005 |
| | | | | 428/323 |
| 2009/0030225 A1* | 1/2009 | Fiorentino | ............ | C07C 67/055 |
| | | | | 558/319 |
| 2010/0158749 A1* | 6/2010 | Benedek | ................. | A61L 9/015 |
| | | | | 422/4 |

* cited by examiner

UNIVERSAL CHEMICAL PROCESSOR

CROSS-REFERENCE TO RELATED APPLICATIONS

The present disclosure relates to commonly-owned U.S. patent application Ser. No. 17/508,427 entitled "FLUIDIZED BED CONCENTRATOR") and Ser. No. 17/508,498 entitled "Advanced Beneficiation Process for Beneficiation, Mobilization, Extraction, Separation, and Concentration of Mineralogical Resources") filed concurrently herewith, both of which are incorporated by reference in their respective entireties.

FIELD OF THE INVENTION

The present disclosure relates to chemical engineering, and in particular relates to a method and apparatus for inducing a wide variety of chemical reactions and processes with lower cost and reducing or eliminating pollution.

DEFINITIONS

Acid Mine Waste: Sometimes also referred to as Acid Mine Water, abbreviated as AMW in both cases. This is ground water that has been contaminated either by run off from a mine or by acidic beneficiation processes in mining operations. This liquid is highly contaminated by a wide variety of chemicals and represents a significant source of pollution.

Actinides: Chemical elements occupying atomic number positions 89 through 103 on the periodic table that are naturally radioactive to varying extents. For the purposes of this document, Radium, atomic number 88, and Promethium, while technically a Lanthanide, which is also a naturally radioactive element, atomic number 61, are included with the Actinides. It is noted that in many cases, these elements are found together in varying ratios, thus complicating subsequent separation processes.

Beneficiation: A process or group of processes that enhance the properties of mineralogical or metallurgical resources to a product suitable for commercial and industrial purposes.

Concentration: A chemical or mechanical process that increases the percentage of an element or compound in a medium by removing the presence of other, undesirable elements or compounds in the medium.

Drier: In the context of this document, the term of art, "Drier" refers to a means of applying thermal energy into a chemical process to remove water or other undesired liquid content from said chemicals. It is noted that the physical components of the drier can also have other functions in a given system so long as appropriate considerations for proper operation are observed.

Dry Chemistry: The term "dry chemistry" as used herein refers to those processes that occur plasmas rather than solutions. They produce fewer pollutants and the remediation is far simpler. It can also be used to refer to other mineralogical beneficiation processes such as crushing, grinding, screening and sorting, which also do not run in liquid baths or produce substantial quantities of pollutants from their operation.

Electromagnetic field: for ease of description, when the term "electromagnetic field" is used alone herein, it means either an electric field alone (E), a magnetic field alone (H), an electrostatic field, or a combination of the above.

Extraction: A chemical process or group of processes that are designed to isolate a specific element or compound from a surrounding matrix.

Feedstock: starting material input to a system which is to be intended to be modified (e.g., separated, chemically altered, decomposed, sterilized) by processes performed by the system. The feedstock can comprise granular solids, liquids, gases or plasma.

Field Enhancement: In the context of this document, the term of art, "Field Enhancement", and its derivatives refer where the presence of such fields enhances some aspect of the reactions carried on within a given apparatus which occur in the presence of intentionally applied electric and magnetic fields.

Flash X-ray Irradiator: A cylindrical large area X-ray source capable of extremely high radiation levels for the purposes of decomposing, sterilizing, or reacting materials within its interior reaction zone. The Flash X-ray Irradiator is the predecessor technology to the RXCP and is described in U.S. Pat. No. 8,019,047 "Flash X-ray Irradiator" (hereinafter '047 patent or FXI). The '047 patent is hereby incorporated by reference in its entirety for any purpose.

Flocculation: A chemical process in which a chemical coagulant is added to a bath and acts to facilitate bonding between particles, creating larger aggregates which are easier to separate. The particles come out of suspension in the form of floc or flake (synonymous terms of art). The action differs from precipitation in that, prior to flocculation, particles are merely suspended, in the form of a stable dispersion in a liquid and are not truly dissolved in solution.

Flotation: A chemical process in which a solution containing one or more desired chemical compounds or elements is mixed with a chemical bath of a specific pH and composition in order to cause the desired chemical compounds or elements rise to the surface where they can be removed by a skimmer or similar apparatus. After flotation, the desired compounds or elements are washed and dried, or sometimes subject to additional wet processes to extract the desired compound or element.

Fluidized Bed: A physical phenomenon that occurs when a fluid (liquid, gas, or plasma) entrains a quantity of a granular solid medium (usually present in a holding vessel) under appropriate conditions to generate a granular solid/fluid mixture that behaves as a fluid, referred to as fluidization of the particulate medium. This is usually achieved by the introduction of pressurized fluid, gas, or plasma, through the particulate medium. This resulting sold/fluid mixture has many properties and characteristics of normal fluids, such as the ability to free-flow under gravity, or to be pumped using fluid type technologies. Fluidized beds are used to facilitate chemical reactions and can also be used to separate materials based on density and particle size.

Fluidized Bed Concentrator: A mechanical apparatus that utilizes aspects of fluidized bed technology to achieve physical separation of a feedstock on the basis of particle size, density or fluidizing medium pressure. Also referred to as FB Concentrator or FB Separator Fluidizing Medium: A granular solid, liquid, gas or plasma which is injected into a Fluidized bed to effect fluidization of the bed medium.

Fluorapatite: The ore from which some fertilizers, phosphoric acid, hydrofluoric acid and phosphogypsum are produced. Its chemical formula is $Ca_5F(PO_4)_3$. It is usually found in combination with Hydroxyapatite $[Ca_5(PO_4)_3OH]$.

Lanthanides: Chemical elements known as the Rare Earths and which occupy atomic number positions 57 to 71 on the periodic table, and Scandium, atomic number 21, and Yttrium, atomic number 39.

Leaching: A chemical process in which a feedstock is mixed with another chemical, typically, but not always a strong acid, base, bacteria, or salt, in order to mobilize a desired chemical. The desired chemical enters solution and is available for subsequent processing steps.

Ligand: A ligand is an ion or molecule that binds to a central atom to form a coordination complex. Ligands in a complex dictate the reactivity of the central atom, including ligand substitution rates, the reactivity of the ligands themselves, and redox. Ligand selection is a critical consideration in most reactions that involve them.

Mobilization: A chemical process which frees a desired element or compound from a complex in a mineralogical resource to enable further beneficiation.

Modulate: to adjust settings of analog equipment, such as analog valves, in a continuous manner (i.e., from fully closed, to partially closed/open to fully open).

Phosphogypsum: A byproduct from the refining of Fluorapatite in the production of fertilizer, phosphoric acid, and Hydrofluoric Acid. Chemically, it is a hydrate of Calcium Sulfate ($CaSO_4.2H_2O$). This material also contains recoverable amounts of Rare Earths (Lanthanides) and some radioactive elements (Actinides).

Phosphoric Acid: The chemical $H_3PO_4$ is used in the production of some fertilizers and also used in many chemical reactions and in the production of some food products, cosmetics and toothpaste.

Plasma: Plasma is the fourth state of matter (other than solid, liquid, gas). It is characterized by having one or more of its electrons removed and it exhibits properties of both liquids and gases. Plasmas are created by a number of means including but not limited to DC excitation, RF (and microwave) excitation, and excitation by means of X-rays, gamma rays and high energy secondary electrons. The current invention is primarily concerned with the use of x-rays as the means of ionization. X-rays are particularly useful as they are at very high energies and thus a single photon can be used multiple times in a given reaction including the generation of high energy secondary electrons, which, by themselves, are useful in stimulating reactions if of high enough energy. It is also the simplest means of achieving total ionization, which is a necessary condition for many of the reactions contemplated by the current invention.

Precipitation: A chemical process in which a solution containing one or more desired compounds or elements is mixed with a chemical bath of a specific pH and composition in a container in order to cause the desired chemical compounds or elements fall to the bottom of the container from which they can be removed by any of several well-known means.

Rare Earths: The group of elements (atomic numbers 57 to 71) including the Lanthanides, Scandium, atomic number 21, and Yttrium, atomic number 39.

Reactive X-ray Chemical Processor: A type of chemical processor designed to enhance reaction conditions by the use of X-ray radiation to ionize species present and promote reactions in a plasma environment. This processor is disclosed in U.S. Pat. No. 9,406,478 entitled "Method and Apparatus for Inducing Chemical Reactions by X-ray Irradiation" (hereinafter '478 Patent, and/or RXCP). The '478 patent is hereby incorporated by reference in its entirety for any purpose.

Screening: The practice of mechanically separating granulated material into multiple grades by particle size using a screen. The screen is a surface with a dense uniform pattern of holes that allows particles smaller than the size of the holes to pass through. Screening can be accomplished using gravitational, vibrational, density, or electrostatic techniques.

Separation: A chemical or mechanical process or group of processes that are designed to isolate chemically similar compounds.

Settling (Sedimentation): A process similar to precipitation in which the desired compounds or elements fall out of a mixture in a container over time (typically due to gravity) but without use of additional chemicals. The desired compounds or elements and then can be collected from the container by well-known means.

Sieving: A subset of screening that is a laboratory procedure in which precision screens are used to sort material based on particle size. The American Society for the Testing of Materials (ASTM) defines screen sizes. These are usually expressed as "mesh" i.e. 200 mesh, 50 mesh, etc.

Stack: Phosphogypsum is normally stored outdoors in a very large pile called a "Stack". Stacks are frequently dozens of acres in sizes and can be hundreds of feet high.

Tailings: Material left over from beneficiation processes of mining operations.

Thickening: As the name implies, thickening is the process where the viscosity of a solution, liquid, slurry, etc. is increased. Some chemical processes work well with low viscosities while others require high viscosities. Thickening provides reliable methods of controlling the viscosity of materials during various stages of processing.

Wet Chemistry: The term "wet chemistry" as used herein refers to those chemical processes that are conducted in a liquid medium and state. As used in the processing of mineralogical ores, tailings, waste products and byproducts, it generally refers to processes that utilize quantities of strong acids, strong bases, amines and biologicals. Wet processes are typically heavily pollution and there remediation is expensive.

BACKGROUND

In many industrial applications, it is necessary to react different chemicals and sometimes to separate them based on chemistry, particle size or density. These processes are traditionally carried out using wet chemistry, frequently involving toxic and polluting chemicals and producing contaminated waste streams and byproducts in addition to the desired end product.

For example, in the mining industry, in order to extract useful mineral resources from the mineral ores, mining operations employ various beneficiation processes to chemically and mechanically separate the desired minerals and elements from others present in the ore. These processes involved include, but are not limited to, leaching, stripping, precipitation, settling, flotation, sedimentation, flocculation, concentrating, mobilization, screening, and thickening. These processes are sometimes referred to as "wet" processes.

Most often, these processes are based on large scale liquid chemistry operations (e.g., in large liquid baths, tanks or ponds) that use toxic and highly polluting chemicals such as strong acids (sulfuric, nitric, hydrochloric, hydrofluoric, etc.), strong alkalines (Caustic Soda (NaOH), Quicklime (CaO), Ammonia ($NH_3$), Soda Ash ($Na_2CO_3$), Limestone ($CaCO_3$), to name a few), concentrated salts (potassium chloride, etc.), various amines and others. While these chemicals can be efficient in producing the desired chemical reactions, during the beneficiation processes the liquids become highly contaminated and are extremely difficult to dispose of in an environmentally sound fashion.

Due to the environmental problems pertaining to wet chemical processes, certain processing activities are no longer, or rarely, performed in the United States, such as Rare Earth processing. Despite the critical importance of the Rare Earth minerals to high technology manufacturing, the United States largely relinquished its globally dominant position in the mining and Rare Earth processing in the 1980's as it proved too difficult and expensive to beneficiate materials containing Rare Earths while maintaining compliance with the governing environmental regulations. China, which has large deposits of Rare Earth minerals, and fewer restrictive environmental regulations, thereafter became the largest processor of Rare Earths. Globally, many companies with significant Rare Earth resources send mined ore China and one or two other countries for processing in order to avoid processing the materials locally and dealing with the toxic byproducts of that activity.

It is only in recent years that an awareness of the need for the United States to return to its position of self-sufficiency in this market. But the state of the art for Rare Earth beneficiation remains the wet chemical processes that are still encumbered with the same set of environmental problems. There is therefore a substantial need for improved process technology, particularly for Rare Earth minerals.

SUMMARY OF THE DISCLOSURE

In a first aspect, the present disclosure provides a Universal Chemical Processor (UCP) that includes a reactor vessel having a central longitudinal axis and main chamber. The UCP comprises a first inlet port for a main feedstock leading to the main chamber, a second inlet port for a fluidizing medium leading to the main chamber, a third inlet port for one or more reactants leading to the main reactor chamber, and a reactive X-ray chemical processor (RXCP). The RXCP includes a hollow cold cathode extending along the longitudinal axis in the main chamber, a grid positioned concentrically and more centrally with respect to the cathode in the main chamber, and an anode positioned concentrically and more centrally with respect to both the cathode and grid. In operation, a fluidized bed can be supported in the main chamber when a fluidizing medium and feedstock are supplied to the main chamber through the first and second inlet ports. When switched on, the cathode of the RXCP emits electrons towards the anode, which, upon impact of the electrons emits X-rays into a radiation zone within the main central chamber of the vessel, the X-rays being capable of ionizing feedstock and reactants, inducing chemical reactions, and sterilizing and decomposing any organic materials within the radiation zone, said processes being available individually, or in various combinations.

In another aspect, the present disclosure provides a method of chemical processing that comprises the steps of configuring a reactor vessel for receiving feedstock, a fluidizing medium and reactants and for supporting a fluidized bed and situating a reactive x-ray chemical processor (RXCP) within the vessel that is operative to emit x-rays in a radiation zone within the vessel.

The fluidized bed can be used for both typical fluidized bed reactive chemical operations as well as separation processes. The fluidized bed can be used separately from, or in conjunction with the RXCP, and the RXCP can be used separately, from, or in conjunction with the fluidized bed.

Numerous additional inventive aspects of the present disclosure are described in the detailed description below.

DETAILED DESCRIPTION

As noted previously, the current practice of the mining industry performs beneficiation using "wet" processes such as Leaching, Flotation, Precipitation, Flocculation, and Settling. These processes typically require large quantities of strong acids (typically sulfuric ($H_2SO_4$), nitric ($HNO_3$), hydrochloric (HCl), hydrofluoric (HF), etc.), strong alkalines (Caustic Soda (NaOH), Quicklime (CaO), Ammonia ($NH_3$), Soda Ash ($Na_2CO_3$), Limestone ($CaCO_3$), to name a few), bacteria, or other salt solutions. At the conclusion of these processes, there is a large quantity of these chemicals left over that is contaminated by a wide array of toxic chemicals which represent a significant pollution threat. It is costly to remediate this waste material, adding to the overall cost of the resulting products. Additionally, beneficiation operations often produce large quantities of contaminated process water which cannot be released without a significant amount of treatment. In sum, the separation and related processes performed by the mining industry are responsible for the generation of a substantial portion of the toxic waste produced by the mining industries, and replacement with a pollution-free alternative would resolve a long-sought problem.

The present disclosure provides a method and apparatus for chemical processing. In a preferred embodiment, the apparatus for chemical processing, referred to as a Universal Chemical Processor (UCP) includes a fluidized bed reactor integrated into a Reactive X-ray Chemical Processor (RXCP). The RXCP, in some operational configurations, can be operated as a Flash X-ray Irradiator (FXI). The UCP can includes additional components for drying and electromagnetic field enhancement. Electromagnetic field enhancement includes using electric, electrostatic and magnetic fields to affect chemical reactions in the UCP via various modes of operation. The UCP thus combines aspects of both fluidized bed, X-ray irradiation and other technologies to achieve a sum that is greater than the parts, and to enable plasma-based processing regimes which were previously not available. The fluidized bed is capable of operating as a reactive chemical processor as well as being able to perform separations on a purely mechanical basis by changing operational control parameters. Individually, each component is capable of a certain range of operations. When combined, in addition to the individual operations, the method and apparatus of the present disclosure enables an unanticipated reduction in process steps and physical plant equipment as a direct result of the combining of multiple individual stages and operations, as discussed below. The present disclosure provides several exemplary processes that can be implemented with the UCP, all of which constitute improvements over traditional approaches directly due to the unique architecture of the UCP.

Figure 1:
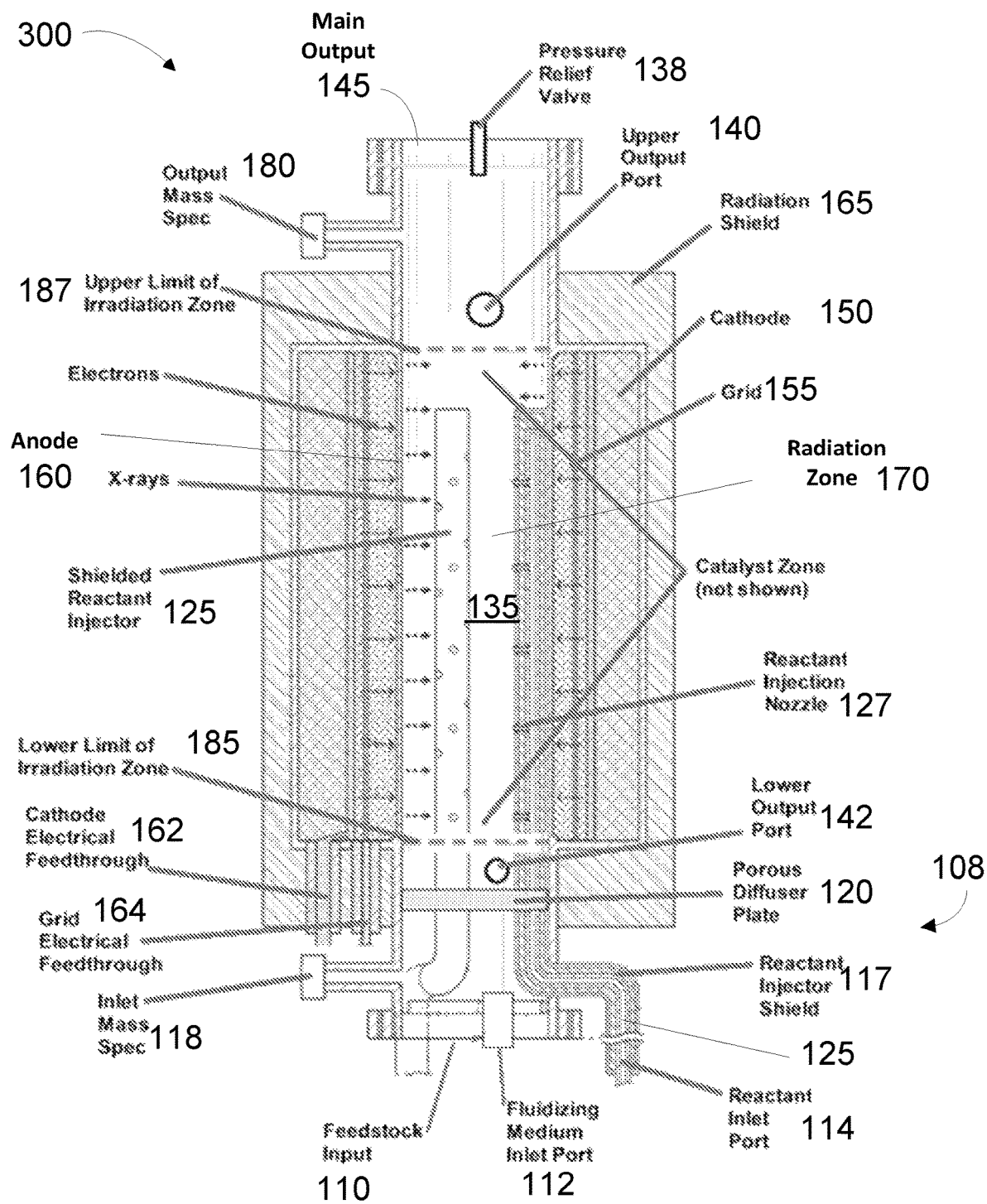
FIG. 1 is a cross-sectional view of an embodiment of the Universal Chemical Processor (UCP) according to the present disclosure.

FIG. 1 is a cross-sectional view of an embodiment of the UCP according to the present disclosure. The UCP 100 comprises a generally cylindrical or columnar vessel 105 in this case having a vertical, longitudinal central axis. It is noted that the UCP can be oriented differently and can have a horizontal or tilted longitudinal axis, although for fluidized bed operations, in most cases, the vertical orientation is preferred. At a base 108 of the vessel 105, which is the lower part as shown in FIG. 1, several input ports are situated that can be welded, molded or fitted to the vessel 105 as known in the art. In the embodiment shown, a feedstock inlet port 110 is coupled to the base 108 of the vessel and provides a conduit through which a feedstock is delivered into the vessel. As the feedstock typically has a larger diameter than other introduced materials, the diameter of the feedstock inlet port 110 has a corresponding size to accommodate the feedstock product. The feedstock comprises a granular solid, liquid, gas, or plasma material which is intended to be processed in the vessel in some manner. For example, the feedstock can be introduced into the vessel in order to undergo one or more chemical reactions, to separate out the components of the feedstock fluid, for reactive chemical processing, catalytic cracking, combustion, heat or mass transfer, product separation, or interface modification (e.g., applying a coating onto solid items). In one advantageous implementation, the feedstock is Phosphogypsum from a waste storage stack, which is a byproduct of fertilizer production, which can include a large number of contaminants including Rare Earths and radioactive elements. The feedstock can be delivered into the feedstock inlet port 110 continuously or in batches (referred to as batch mode), and the contaminants can be separated out for further processing or for use as is. The feedstock can also be delivered using other ports such as the reactant injector ports.

A fluidizing medium inlet port 112 is positioned adjacent to the feedstock input port at the base 108. A fluidizing medium is delivered into the vessel 105, typically at higher than atmospheric pressure, through the fluidizing medium inlet port 112. The fluidizing medium is introduced under pressure across the bottom of the reactor. The fluidizing medium can comprise a uniform gas such as compressed air, or a uniform liquid such as water. Alternatively, the fluidizing medium can include a mix of gases, plasma, or liquids. A wide range of liquids and gases can be used depending on the intended process. As an example, nitrogen or argon can be used as the fluidizing medium in lieu of compressed air if the material being processed (e.g., separated) can be adversely affected by the present of oxygen. Various plasmas may be used as well with the effect of causing additional reactions to occur. The choice of fluidizing medium is dependent on the desired end product. Preferably, the fluidizing medium port and injector is shielded against X-ray irradiation. The shielding can be implemented by forming the inlet port using concentric pipes layered with filler material composed at least in part of a material resistant to X-ray radiation such as lead. An isolation valve (not shown in FIG. 1 for clarity) can be coupled to the fluidizing medium inlet port 112 open, close or modulate the flow of the fluidizing medium when not needed.

In addition to the feedstock and the fluidizing medium, additional reactants for promoting one or more chemical reactions, heat transfer, catalysis or otherwise can be introduced into the vessel via one or more reactant inlet ports 114 also situated at the base 108. Like the fluidizing medium port, the reactant inlet port 114 is preferably shielded against X-ray irradiation. In one embodiment, the reactant inlet port is surrounded by a shield 117 that can be formed of concentric pipes with filler material between the concentric pipes composed at least in part of a material resistant to X-ray radiation such as lead. The outer pipe should be constructed of a material that will not react with the other materials present in the reaction zone such as 316 steel or titanium. In the depicted embodiment, unlike the feedstock and fluidizing medium inlet ports 110, 112, reactant inlet port does not deliver reactants into the base of the vessel, but rather the reactant inlet port leads to a reactant injector 125 having a plurality of outlet nozzles e.g., 127 positioned at various heights in the vessel. The shield 117 allows reactants to be introduced without their being ionized until they are in the reaction chamber 135 and are introduced into the reaction zone in a uniform fashion. In some implementations (not depicted), the feedstock inlet port 112 can be configured similarly to the reactant inlet port to introduce material into the middle of the chamber 135, preferably with fewer nozzles, each nozzle having a larger diameter than those of the reactant inlet nozzle.

Figure 2:
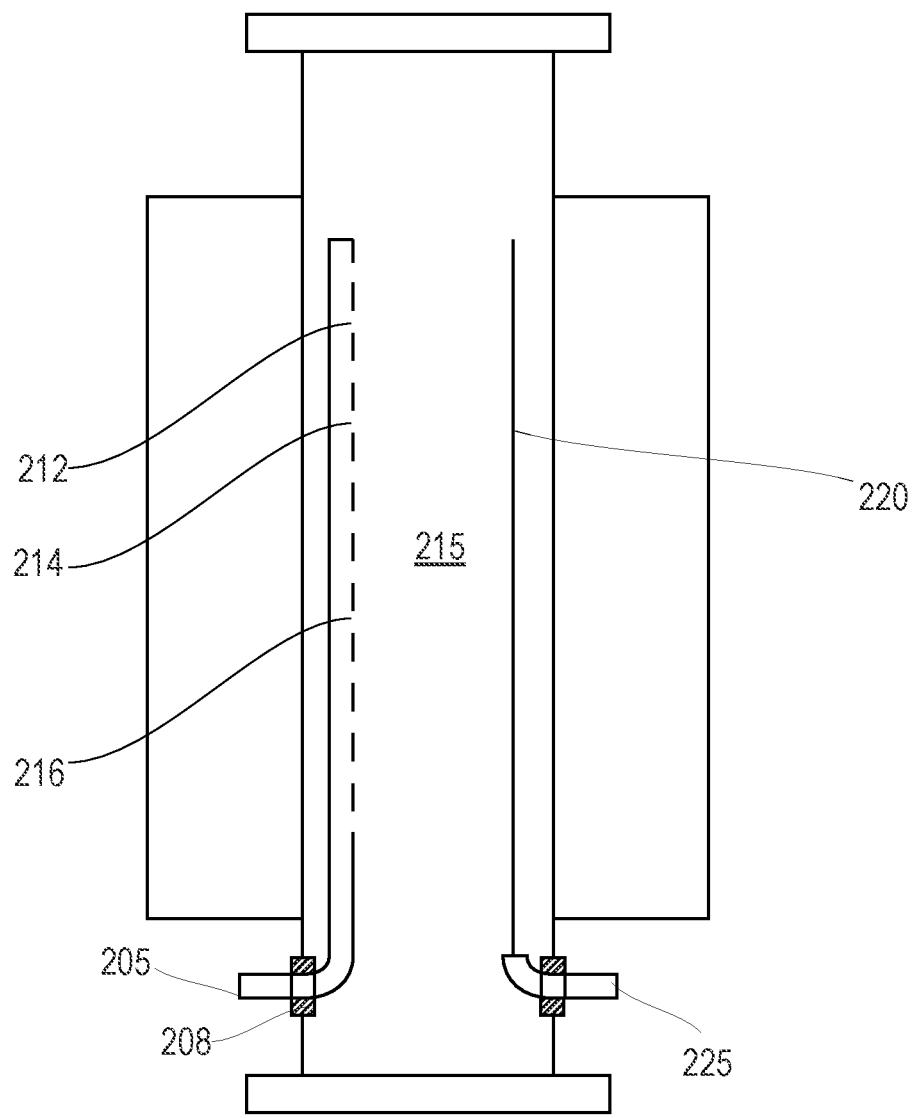
FIG. 2 is a simplified, schematic cross-sectional view of a UCP according to an embodiment of the present disclosure showing an exemplary electrode configuration for plasma enhanced Fluidized Bed without X-ray.
Figure 3:
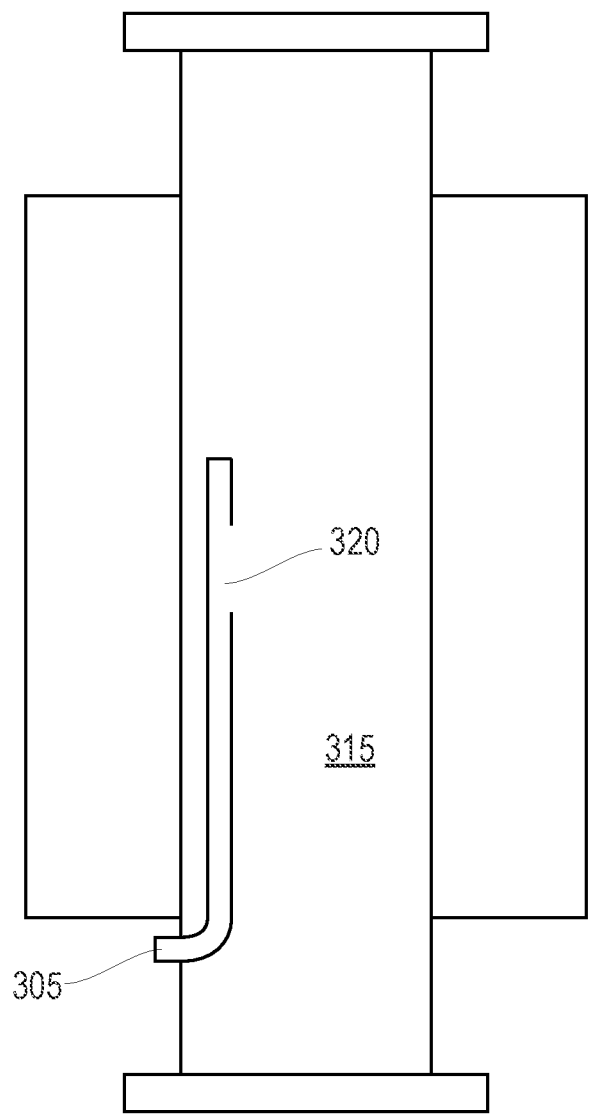
FIG. 3 is a simplified, schematic cross-sectional view of a UCP plan according to an embodiment of the present disclosure showing an exemplary Reactant Injector modified for use as a feedstock injector for fluidized bed operation FIG. 4. is a simplified, schematic cross-sectional view of a UCP according to an embodiment of the present disclosure showing an exemplary arrangement of catalysts in the UCP.

FIG. 2 is a schematic cross-sectional view of an embodiment of a UCP showing an insulated reactant inlet injector 205 that can be coupled to the housing of the UCP with an insulated feedthrough 208, which can be made from ceramic material. The injector 205 is a shielded conduit that extends longitudinally into the main chamber 215 of the UCP. Reactant transported through the reactant injector exit in the reaction zone within the main chamber through the plurality of nozzles e.g., 212, 214, 216. FIG. 3 is a schematic cross-sectional view of an embodiment that includes a shielded injector 305 adapted for feedstock delivery that also extends longitudinally into the main chamber 315 of the UCP. In contrast to the embodiment shown in FIG. 2, materials transported through shielded injector 305 exit through a single large nozzle 320 into the reaction zone within the main chamber of the UCP.

In some embodiments, the UCP includes an electrode within the main chamber 135 that is adapted to either generate a plasma or an electromagnetic field within the main chamber or to maintain a plasma that has been input to the vessel. The plasma can be used to induce chemical reactions in the fluidized bed and to [any other effects or uses of plasma. In FIG. 2, an electrode 220 in the shape of a rod that extends through the reaction zone in the main chamber 135 is shown. The electrode is coupled to a power supply (not shown) via an insulated feedthrough 225 which can also be made from a ceramic material. The power supply may be AC, DC, or RF, depending on the particular type of plasma, electromagnetic field and biasing that is desired. The voltage of the electrode can range from as little as 2-20 Volts up to many KiloVolts depending on a number of factors including the density of the plasma, the composition and density of the feedstock and reactants in the reaction zone, and the pressure of the plasma. Essential to the successful implementation of the plasma or field enhancement is that attention be paid to the voltage ratings of the insulators, and to the shape and spacing of the electrode structures from the wall or other grounded objects such as catalysts, etc.

Figure 6:
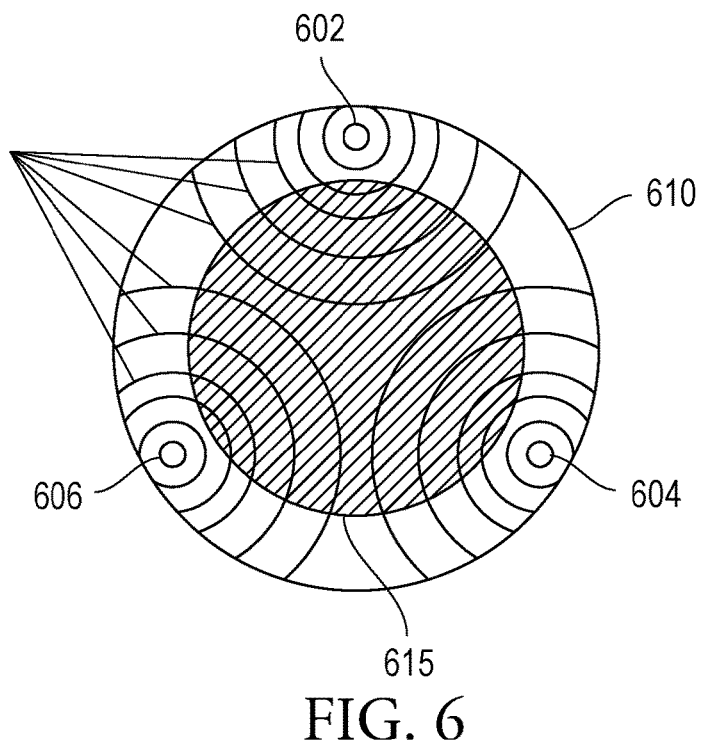
FIG. 6 is a cross-sectional view of a UCP according to an embodiment of the present disclosure in which plasma generated in the UCP are confined using electrostatic field enhancement.
Figure 7:
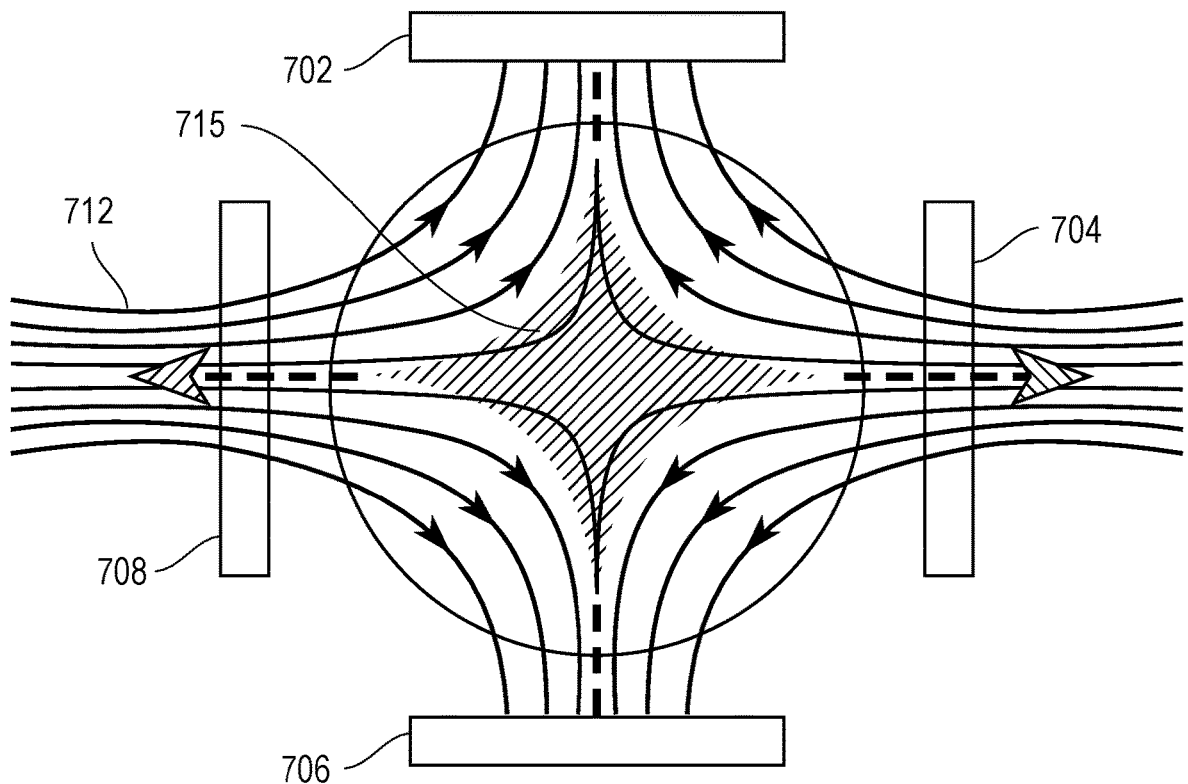
FIG. 7 is a cross-sectional view of a UCP according to an embodiment of the present disclosure in which plasma generated in the UCP are confined using electromagnetic field enhancement.

It is desirable to keep the plasma from touching the walls of the UCP reaction zone, which is referred to as "containment." This may be accomplished by use of either electrostatic or electromagnetic means. In the preferred electrostatic embodiment, a plasma can be generated without use of X-rays by internal electrostatic fields as shown in FIG. 6 (discussed below) in which electrodes similar to the electrode 220 shown in FIG. 2 are employed. In other embodiments, external electromagnetic coils can be used to create a magnetic field within the RXCP reaction zone area as shown in FIG. 7 (discussed below). There are many field configurations, both electrostatic and electromagnetic that will work to provide the desired isolation of the plasma from the chamber wall. These will be apparent to the person of ordinary skill in these arts.

Returning to FIG. 1, ports 118, 180 at the input and output ends of the UCP lead to mass spectrometers. This allows a real-time analysis of the feedstock material both before and after its being processed by the UCP. The fluidizing medium and feedstock supplied into the vessel combine and are forced through a diffuser plate 120 positioned above but proximally to the base of the vessel. The diffuser plate 120 can be made from a variety of radiation resistant materials, so long as they are appropriately porous. Alternatively, the diffuser plate can have a uniform pattern of holes to achieve the same effect. The diffuser plate 120 has the effect of distributing and increasing the uniformity of the fluidizing medium as it enters the main chamber 135 of vessel at which separations and/or other processes take place (referred to as the "separation region" when the fluidized bed is being operated to separate feedstock materials). A recirculating pipe 138 takes the flow of the fluidizing medium from the top of the chamber, runs it through a recirculating pump, and reapplies it to the bottom of the chamber via a recirculation loop (not shown in FIG. 1), mixing it with the incoming fluidizing medium.

Figure 4:
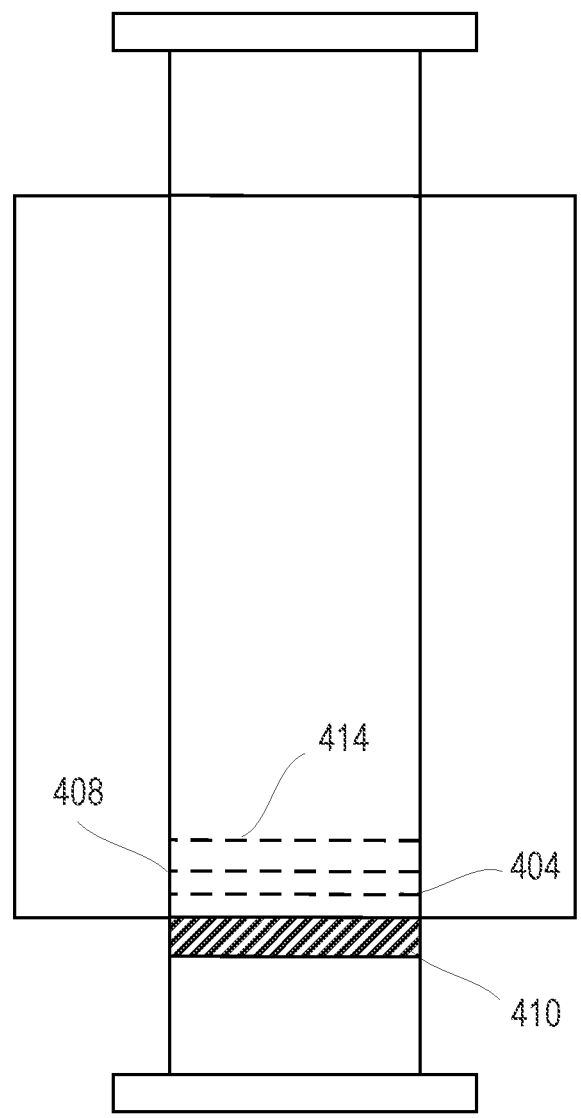

In some implementations, catalysts may be located above the diffuser plate. However, more generally, catalysts can be located in different locations within the reaction zone; different locations provide different chemical results in the output. For example, in some cases it is desirable to have the catalyst at the beginning of the reaction zone, as shown in FIG. 4, but catalysts also be positioned centrally, near the top end of the reaction zone, or outside the reaction zone entirely. The location depends on the degree of catalysis desired. While catalysts come in many forms, for clarity, their implementation as one or more screens is shown in FIG. 4. In this exemplary embodiment, two catalyst screens 404, 408 are positioned above a diffuser plate 410 and below the lower limit of the reaction zone 414 in the main chamber of the UCP (the reaction zone is explained with reference to the RXCP section the UCP below). It is noted that while two screens 404, 408 are depicted there can be a single screen or a larger number of similar screens. The screen implementation is one common method of introducing the catalyst into reactions generated in the UCP. Other forms of introducing catalysts include plates, trays, meshes and various types of porous containers. In some implementations the diffuser plate 410 can be used to carry the catalyst. Introduction of other forms of catalysts will be apparent to a person of ordinary skill in this area.

In some embodiments, a specific category of catalysts known as electrocatalysts can be used in the beneficiation process. Electrocatalysts function at electrode surfaces or, most commonly, can be incorporated in the electrode surface itself. An electrocatalyst can be heterogeneous such as a platinized electrode. This is achieved by mounting the catalyst on an electrically insulated structure (not shown) and providing an electrically insulated electrical feedthrough to allow a voltage or signal to bias the catalyst, thus creating an electrocatalyst. Homogeneous electrocatalysts, which are soluble assist in transferring electrons between the electrode and reactants, and/or facilitate an intermediate chemical transformation described by an overall half reaction. Homogenous electrocatalysts can be employed for certain types of reactions, but are not appropriate for all reactions, as they can suffer from physical instability and solubility. Electrocatalytic action can be stimulated either by a direct electrical connection or by interaction with electric fields within the reactor vessel.

The feedstock material becomes entrained in the fluidizing medium in the main chamber 135 and the resulting combination of granular solid and fluid (including gases and plasmas) behaves as a fluid (i.e., undergoes fluidization) under certain controlled conditions. Fluidization occurs when various factors and parameters, including the dimensions of the vessel, the pressure drop across the bed, the average particle density, feedstock, and reactant flow rates, and other factors (discussed below) have magnitudes that are designed to cause the feedstock and fluid mixture to behave as a fluid. In the depicted embodiment, this is achieved by the introduction of pressurized fluidized medium through the particulate medium at the base of the vessel of an appropriate diameter. The combined granular solid/fluid medium, referred to as the fluidized bed, is a suspension, and has many of the properties of normal fluids, such as the ability to free-flow under gravity, or to be pumped using fluid-type technologies. It is this aspect of fluidized beds that allows horizontal operation. A recirculation pipe 138 receives the pressurized fluidizing medium the top of the chamber, applies pressure to the fluidizing medium via a pump 161 medium and reapplies the fluidizing medium at the bottom of the chamber at a reentry port 163, mixing it with the incoming fluidizing medium. As noted above, additional fluidizing medium incoming from inlet port 112 can be cut off when need via isolation valve (not shown in FIG. 1). However, additional fluidizing medium is typically need to offset volume loss and maintain constant pressure within the FB concentrator as product is removed.

Within the chamber 135, the upper surface of the bed is relatively horizontal but can be wave-like in nature, which is analogous to hydrostatic behavior. The bed can be considered to be a heterogeneous mixture of fluid and granular solid that can be represented by a single bulk density. Inside the fluidized bed, larger and denser particles tend to move downwards in the bed while smaller, lighter particles tend to move upwards, exhibiting fluid behavior in accordance with Archimedes' principle. As the density (more precisely, the solid volume fraction of the suspension) of the bed can be altered by changing the fluid fraction, objects with different densities in comparison to the average density of the bed can be caused to sink or float. The upwards force of the fluidizing medium is a strong contributor to the upward motion of the particles.

In fluidized beds, the contact of the solid particles with the fluidization medium is greatly enhanced when compared to packed beds. This behavior in fluidized combustion beds enables a high degree of thermal transport inside the system and heat transfer between the particles and the fluidizing medium. The enhanced heat transfer enables thermal uniformity analogous to that of a well-mixed gas, and the fluidized bed can have a significant heat-capacity while maintaining a homogeneous temperature field. As noted above, in a fluidized bed, the denser materials tend to go to the bottom of the FB. It should be noted that very small dense particles can move to the top of the FB. This creates a need for a further separatory operation. This is due to a simple gravitationally induced process. As an example, if air is used as the fluidizing medium, the flow upward through the bed of materials causes the material in the bed to essentially float on the fluidizing medium. When the material is floating, it means there is sufficient pressure to fluidize the whole column and push the lighter materials towards the top of the column while the denser portions of the material stay at or move to a lower elevation in the column.

The condition for fluidization can be presented by equation (1) below in which the apparent pressure drop multiplied by the cross-section area of the bed is equated to the force of the weight of the granular solid particles (less the buoyancy of the granular solid in the fluid).

$$\Delta p_w = H_w(1-\varepsilon_w)(\rho_s - \rho_f)g = [M_s g/A][(\rho_s - \rho_f)/\rho_s] \quad (1)$$

in which $\Delta p_w$ is the bed pressure drop, $H_w$ is the bed height, $\varepsilon_w$ is the bed voidage, (i.e. the fraction of the bed volume that is occupied by the fluid spaces between the particles), $p_s$ is the apparent density of bed particles, $\rho_f$ is the density of the fluidizing fluid, g is the acceleration due to gravity, $M_s$ is the total mass of solids in the bed, and A is the cross-sectional area of the bed.

Additionally, the introduction of the fluidizing medium into main chamber 135 has the effect of creating bubbles which form as a result of physical interactions with particles of the feedstock material and pressure differentials. In a physically small bed, the bubbles formed are small and sometimes microscopic. In a large-scale industrial bed, which can be ten to fifteen feet in diameter, the bubbles can be quite large. The bubbles increase the mixing of chemicals in the fluidized bed. A means of venting the pressure (e.g., a relief valve) 138 is included at the top of the vessel to allow a constant differential pressure environment to be maintained within the bed. Pressure relief is preferably achieved by means of recirculating piping, particularly when the fluidizing medium is reused. When a given bubble or molecule of air reaches the upper region of the bed, velocity of the air suddenly drops by almost factor of 10 due to the increase in diameter of the bed. This means lighter (less dense) particles will collapse back into the turbulent region where they recirculate and eventually reach a height in the bed that is stable, based on the particle size, density and fluidizing medium pressure. It is noted that fluidized beds can be run at atmospheric pressure, positive pressure, or under partial vacuum.

A variety of material mixtures can be separated using the fluidized bed. And as noted, gases, liquid, granular solids or mixed gases can be utilized as the fluidizing medium. Specific materials and fluidizing means are chosen as appropriate to the specific task at hand. If batch-oriented processing is intended, the fluidized bed method can achieve high levels of separation by running the process for an extended period of time. If, however, a continuous process is desired, such as is typically found in industrial scale applications, then the fluidized bed may be modified to include means for continuously introducing a material to be processed, and a means to remove the separated materials of differing densities. Multiple stages comprising multiple fluidized beds in distinct vessels may be required to achieve the desired degree of processing and/or separation.

The separation processes performed by the fluidized bed is intended to be a substitute for flotation, settling, some precipitation, and sedimentation processes typically found in industrial, mining, and laboratory chemical processes. The most significant advantage is that the separation is performed without the use of large quantities of toxic and environmentally unsound chemicals. The separation proceeds due to the properties of the fluidized bed, which thoroughly mixes the component feedstock materials and effectively segregates the materials by density over a period of time. The lower and upper outputs, 124, 128 can have mass spectrometers or other analytical instruments connected to them so that an online analysis of the separation streams can be performed with the FB concentrator while operating.

Figure 8:
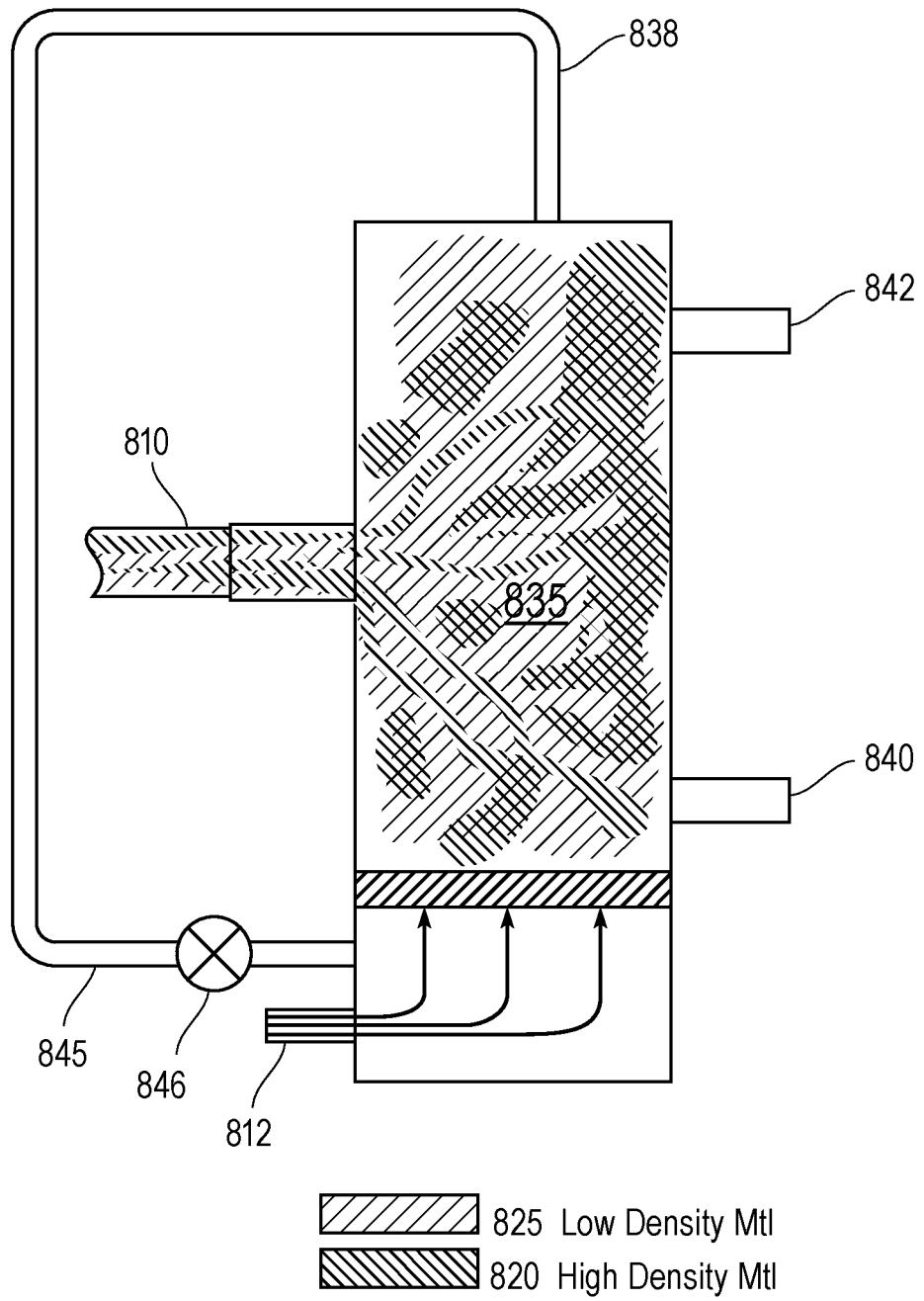
FIG. 8 is a schematic cross-sectional view showing a first stage of a separation process according to the present disclosure using the fluidized bed operation of the UCP.
Figure 9:
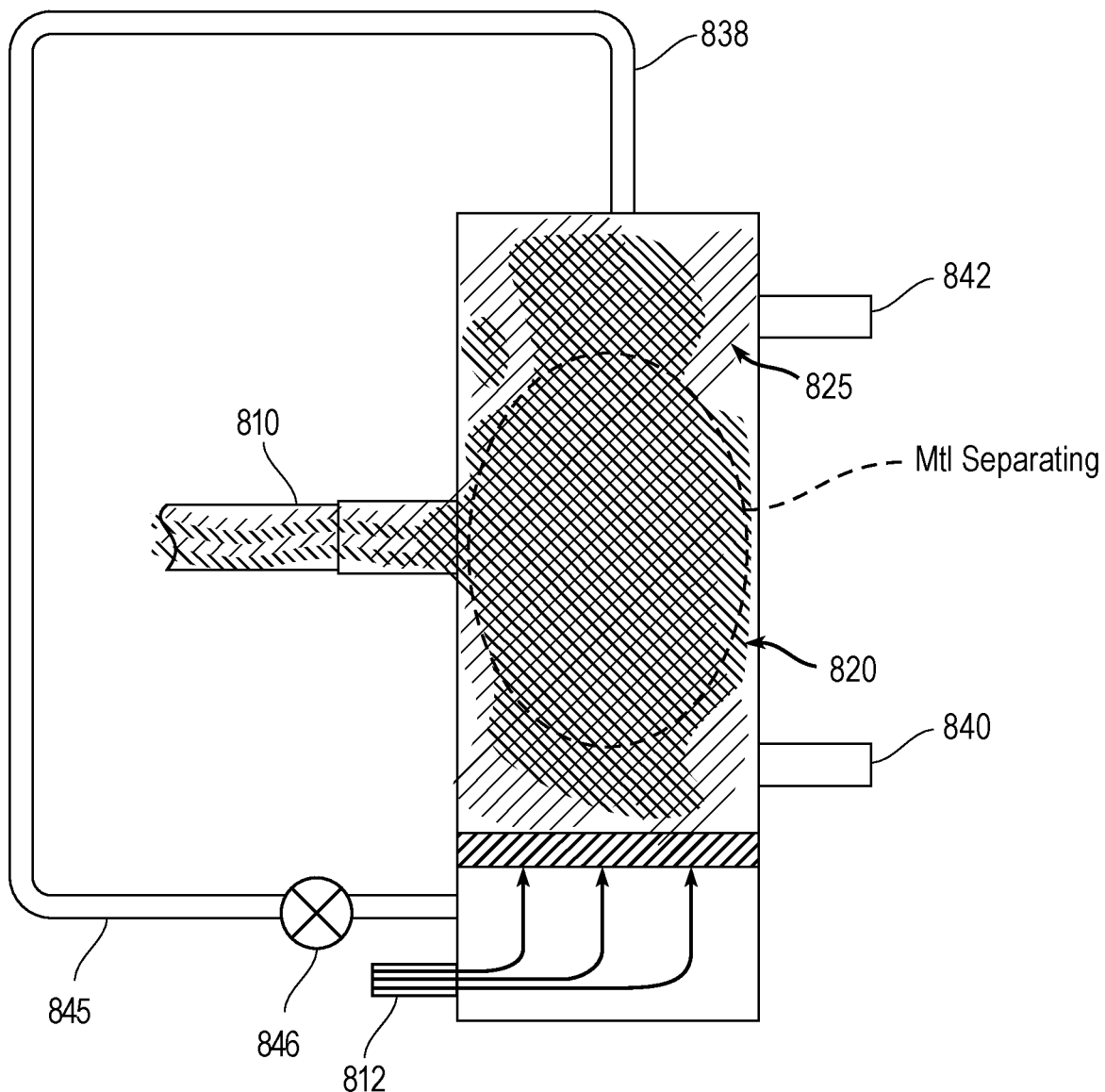
FIG. 9 is a schematic cross-sectional view showing a second stage of a separation process according to the present disclosure using the fluidized bed operation of the UCP.
Figure 10:
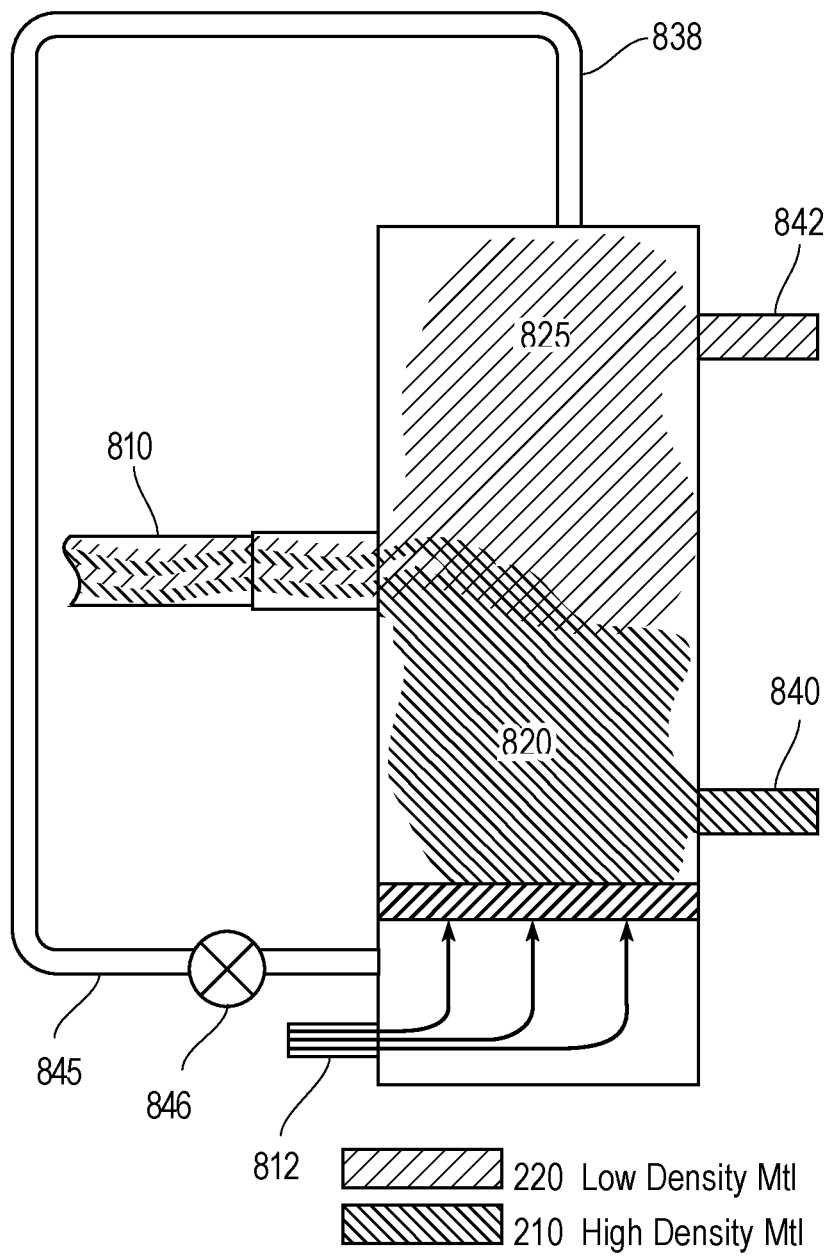
FIG. 10 is a schematic cross-sectional view showing a third stage of a separation process according to the present disclosure using the fluidized bed operation of the UCP.

FIGS. 8-10 show stages of an exemplary sequence of a separation process according to the present disclosure using the FB Concentrator function of the UCP. In FIG. 8, a feedstock containing mainly first and second components (components A and B) of different densities enter through the feedstock inlet 810 into the main chamber 835 (separation zone) of the UCP in which a fluidized bed is maintained through the supply of the fluidizing medium through fluidizing medium inlet 812. In the example shown, component A is denser than component B. As shown in FIG. 8, as the feedstock material enters the main chamber 835, the feedstock material initially diffuses out in a generally random fashion into the volume of the chamber.

By the second stage shown in FIG. 9, the feedstock material has spread throughout the volume of the fluidizing bed and has begun to separate out into a first partially separated mixture 820 located toward the bottom of the main chamber at which the denser component (A) is concentrated at a higher level relative to the feedstock and into a second region 825 located toward the top of the main chamber at which the less dense component (B) is concentrated at a higher level relative to the feedstock. At the second stage shown in FIG. 9, the separation process is in an early or intermediate point. A concentration gradient has begun to form, but the components have not been completely separated.

At the third stage shown in FIG. 10, components A and B have separated more fully and the regions 820 and 825 contain substantially one component or the other (i.e., there is very little of component A in region 925 and very little of component B in region 920). At this point the lower and upper outlet ports 140, 142 are opened to allow a separated output. A fluid with a high concentration of component A flows out of the vessel through the lower output 840, and a fluid with a high concentration of component B fluid out of the vessel through the upper output 842. As noted above, the output streams at outlet ports 840, 842, while greatly concentrated relative to the input feedstock may not be sufficiently concentrated for desired purposes and the outputs can be input to further UCPs, fluidized bed concentrators or processing devices to further separate out or otherwise process the components. Additionally, as noted above, the fluidizing medium is recirculated via recirculation pipe 838 and pump 846 to maintain the volume and pressure of the fluidizing medium in the fluidized bed.

In one example, the UCP can be used to remove Actinide elements from mineralogical feedstock materials. The UCP can be operated in fluidized bed mode (in one or more stages) to separate out relatively Actinides from the feedstock such a Uranium, Radium, Thorium, etc. This enriched output material can be dried using a microwave oven or other drying apparatus. The relatively light materials output from the fluidized bed can be to a UCP operating in RXCP mode in which the materials undergo chemical reactions in the presence of ammonia ($NH_3$). This step replaces conventional wet leaching in the presence of manganese oxide ($MnO_2$). The products of the reaction in RXCP mode can output to a further fluidized bed stage which again separates the products according to density. The denser output from the second fluidized bed stage is typically enriched in residual Actinides such as Radium. This additional output can be dried for convenient non-polluting removal.

The fluidized bed separation process can be enhanced by the use of screening both before and after the fluidized bed operation. Screening involves mechanically separating granulated material into multiple grades by particle size using a screen. Screening enables the number of fluidized bed stages can be reduced, leading to additional improvements in cost, footprint, safety and throughput.

In one important application, the fluidized bed can be used as a means of separating materials on the basis of their density in the beneficiation of Lanthanides and Actinides. Because there are no chemical reactions involved in the basic fluidizing bed separation, the fluidized bed can be implemented in a simpler manner than that usually found in the chemical industry, for example the fluidized beds used in the manufacture of polyethylene.

Historically, fluidized beds have been operated using granular solids, liquids, and gases. The current inventors have realized that it is possible to also operate a fluidized bed using a plasma as the fluidizing medium in the bed or having a plasma in the presence of another fluidizing medium in the bed. There are examples of other plasma processes where plasmas are flowed into a chamber at some rate to achieve a desired end result. One such example is the Plasma Wind Tunnel which is used to simulate re-entry of satellites into the atmosphere and the plasma conditions that they are subject to in that circumstance to verify that the satellite will burn up upon re-entry. The present invention brings a plasma, which in many ways behaves as a gas, into the chamber through the appropriate inlet port 114, and paying attention to not grounding out the electrical charge of the plasma by providing an insulating means to keep the plasma isolated from ground. The plasma, once inside the reactor, behaves much as a gas would, but also behaves as it does in the RXCP mode. The impact of this is substantially increased reaction rates and reduced residence times in the reactor.

Figure 5:
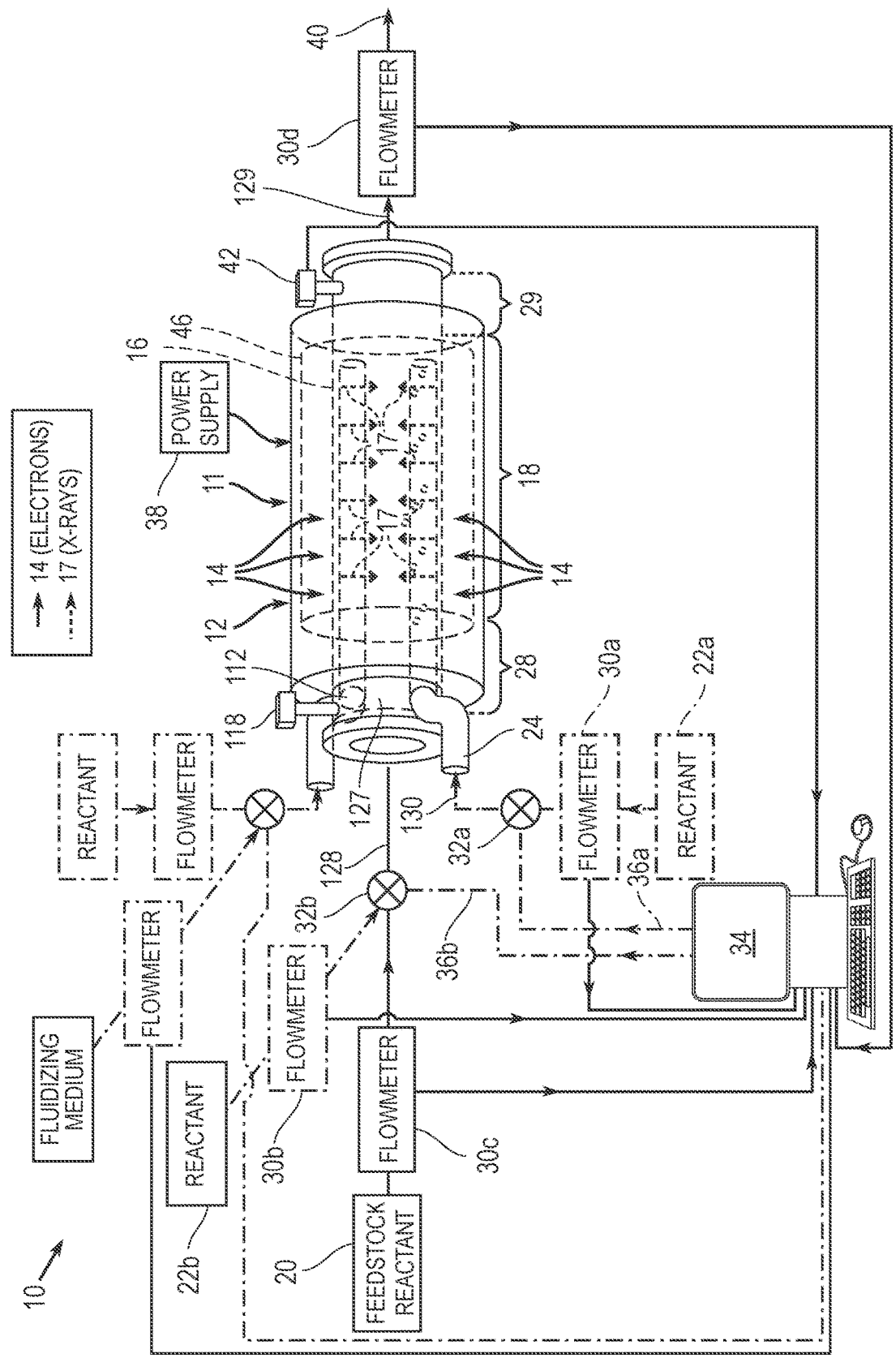
FIG. 5 is a schematic diagram showing an embodiment of a system including the UCP and a control system according to the present disclosure.

It may be desirable to include insulated electrodes that can have a bias voltage applied to them to maintain the plasma or electromagnetic field in the fluidized bed when there is no X-ray present. This may be accomplished by means of a separate electrode in the reaction zone 170 or by using the outer shell of the reactant injectors as the electrode and providing an insulation means for the reactant injectors where they enter the reactor to keep them isolated and above ground potential. Different electrode configurations are shown in FIG. 5.

Returning again to FIG. 1, when the feedstock material is separated by density, lighter components are removed via an upper output port 140 (or a plurality of such ports) positioned at or near the top of the main chamber 135 and heavier components are removed from a lower output port 142 (or plurality of such ports) positioned toward the bottom of the main chamber above the diffuser plate 120. The height of the port and particle size density determines the density of the material being removed. The separated material is pushed out of the fluidized bed through the output ports 140, 142 by the internal pressure within the bed. The output ports 140, 142 are connected to subsequent portions of the process which can vary widely depending on the material being processed. In addition, there is a main output port 145 positioned at the top of the reactor for non-FB processes such as chemical production. The The fluidized bed of the present disclosure is intended to be a substitute for flotation, settling, some precipitation, and sedimentation processes typically found in industrial, mining, and laboratory chemical processes. The most significant advantage is that the separation is performed without the use of large quantities of toxic and environmentally unsound chemicals. The separation proceeds due to the properties of the fluidized bed, which thoroughly mixes the component feedstock materials and then effectively segregates the materials by density over time.

It is noted that the UCP can be operated as a fluidized bed alone or in conjunction with the Reactive X-ray Chemical Processor (RXCP) plasma-generating processes, field-enhancement and drying. The fluidized bed, plasma-generation, field-enhancement can be employed simultaneously in a UCP vessel or sequentially in various combinations, either in the same unit in a batch processing environment, or in separate units in a continuous processing environment.

In FIG. 1 the middle section of the UCP includes elements of a Reactive X-ray Chemical Processor (RXCP) that can totally or partially ionize (to any desired state) chemical reactants introduced into the vessel. Embodiments of a standalone Reactive X-ray Chemical Processor (RXCP) are disclosed in commonly owned and assigned U.S. Pat. No. 9,406,478, entitled "Method and Apparatus for Inducing Chemical Reactions by X-ray Irradiation." These capabilities are further enhanced by the addition of both electromagnetic and electrostatic field sources which provide the ability to conduct reactions under the influence of these fields which will enhance certain reactions. Additionally, the UCP can include a drier for removing water or other undesired liquid content from inputs or reaction products.

The basic process of the RXCP section starts with the total or partial ionization of all or part of the feedstock reactant which is input through a feedstock inlet 110, and all other reactants, input through one or more radiation-shielded reactant injectors 114, 116. This causes the feedstock and reactants to be rendered into a plasma. This is then followed by recombination of the resulting mix of atomic species into their lowest energy states. The ionized feedstock and reactants within the reactor are rendered into a plasma state. The resulting mix of atomic species produces an output flow. The RXCP section uses a cylindrical cold field emission hollow cathode 150, a hollow grid 155, and a hollow anode 160 transmission-type X-ray source in conjunction with reactant measuring, control, and injection systems (not shown in FIG. 1) located in the central region of the device. The cold field emission cathode 150, a grid 155 that together comprise an electron gun. The structure of the transmission x-ray tube starts with a hollow cathode 150 within which there is a coaxially oriented hollow grid 155, within which there is a coaxially oriented hollow anode 160, all arranged such that their central axes are coincident. The electron gun of the RXCP can achieve a theoretical maximum current density of approximately 80,000 Amps/cm$^2$ in the pulse mode, which ultimately allows high levels of irradiation due to the high fluence created by the large number of electrons used to create the X-ray beam. In practical applications, the cathode 150 is not loaded to its theoretical maximum, but rather to some lesser value. For instance, the RXCP section of the UCP can achieve high X-ray photon energies of typically 0.025-5 MeV, and a high beam current that can typically range from KiloAmps to many MegaAmps. The RXCP section can operate at lower current levels, which are dependent on the fluence requirements of the specific reaction.

In operation, the cathode 150 is charged using a power supply (not shown in FIG. 1) which meets the voltage, current, and, if used in the pulse mode, risetime and pulse repetition-rate requirements. A bias resistor (also not shown) is connected between the cathode 150 and the grid 155 and is used to create a voltage on the grid 155 so that the tube is normally in a standoff condition (not conducting). When a control signal of ground potential is applied to the grid 155, the grid releases control of the cathode 160 and the cathode discharges. Electrons then travel from the cathode 150 to the anode 160. When they strike the anode 160, they generate X-radiation and secondary electrons. The X-rays and secondary electrons are liberated from an X-ray emitting (inner) surface of the anode 160 in an isotropic fashion. Due to the relatively thin wall of the hollow anode 160, a substantial portion of the x-rays and secondary electrons generated (about 50%) propagate into the central region of the hollow anode. The penetration depth of the incident electrons is controlled by the balance between the cathode voltage and the thickness of the anode 160. The anode 160 typically has a thin wall section in the region of the irradiation volume to achieve a degree of control over the desired transmitted irradiation. The anode wall section thickness is a function of the diameter of the interior space, the cathode voltage, and the atomic number (Z) of the anode. The secondary electrons released from the anode play an important role because they dramatically increase the number of potential reactions. Each liberated secondary electron can, in turn strike atoms within the anode, causing further X-ray emission and release of additional secondary electrons. This cascade effect of the secondary electrons helps ensure that a realistic energy balance can be achieved. Cathode voltage is supplied through cathode electrically insulated vacuum feedthrough 162, and grid voltage is supplied through grid electrically insulated vacuum feedthrough 164. Both feedthroughs 162, 164 are electrically insulated and high vacuum sealed, and penetrate the biological radiation shield 165 and vessel housing.

Other radiation sources can be used instead of a cold cathode field emission X-ray source. An alternative is to use a plurality of conventional X-ray sources. It is also possible to use a nuclear radioisotope source if it has a suitable hollow cylindrical geometry, an appropriate gamma radiation output, and half-life. The entire UCP apparatus is surrounded by a radiation shield 365 whose thickness is commensurate with the X-ray (or gamma) energies generated.

The X-rays generated by the RXCP section enter the central portion of the main chamber 135 in what is termed as a radiation zone 170 which is spatially delimited within the vessel by a lower limit 185 and upper limit 187. Within the radiation zone, compounds and atoms preset are partially or totally ionized into the constituent molecules into ions of the atomic species present by the mixture of X-ray photons and secondary electrons formed by the gun and other collisional interactions within the reaction zone. Concurrently and synchronously with this, secondary, tertiary and additional reactants can be injected into the reaction space and totally ionized, either simultaneously or sequentially. There is significant intentional turbulence in the radiation zone to ensure complete mixing and interaction of any ions, electrons, atoms, and molecules. It is possible and frequently necessary to include catalysts in the radiation zone to enhance specific properties of a reaction. In most cases this will be the lowest energy state compound unless specific measures are taken to change that. The natural tendency of this system is to produce lowest energy state compounds. By adjusting the various parameters, it is possible to determine exactly what molecules will emerge once recombination is allowed (by the cessation of the X-ray flux). A number of adjustable parameters are used to control the type of reaction and the chemical reaction rates that take place. The adjustable parameters include: 1) X-ray voltage; X-ray current; X-ray pulse duration (in either pulse or continuous mode); Ratio of first and second (and subsequent, if any) reactants; Flow rates of reactants through the reactor, and Specific chemicals chosen as reactants; the use of catalysts, etc.

Reactants are introduced into the main chamber via shielded reactant injector(s) 125 through which they enter the reaction zone of the main chamber 135 through the shield reactant injector(s) 125. Although multiple reactant injectors can be employed, multiple reactant species can be introduced through a single reactant injector. It is noted that the injection ports can be made large to allow for substantial amounts of reactant to flow into the radiation zone 170, as would be desirable for some fluidized bed applications (See FIG. 3). The number of injection ports can be as low as desired.

To preserve the molecular structure of reactants prior to injection, it is necessary to provide an X-radiation shielded injection means. This prevents premature dissociation, or premature partial or total ionization, of the injected reactant prior to one or both of introduction of the feedstock material into the irradiation volume 170 and introduction of reactant. The requirements for a shielded injection means are preferably met by implementing the reactant conduit 125 using concentric pipes with an X-ray radiation shielding material 117, which is typically lead or another high atomic number element, filling the interstitial space between the concentric pipes. The pipes can be made of stainless steel or some other non-reactive material that is compatible with, and not affected by, the feedstock and reactants input via inlets 110, 114 or the radiation environment in irradiation volume 170. The reactant inlet port 114 leads to a shielded reactant injector 125, which is a generally cylindrical conduit having nozzles, e.g., 127. FIG. 1 also includes a plan (non-cutaway) view of another shielded reactant injector (the UCP can include one, two or more shielded reactant injectors) showing a distribution of nozzles positioned circumferentially around the injector conduit, the number of reactant injectors being dependent on the requirements of the intended reaction.

It is noted that additional electrodes, either in the form of discrete electrodes or in the form of electrically insulated shielded reactant injectors can be included here for plasma support and field enhancement, or external magnetic coils can be provided for plasma confinement or field generation. It is possible to have both conditions supported, but such a configuration would be functionally redundant.

Both feedstock materials and reactants enter the main chamber 135 and are exposed to X-rays and secondary electrons. If a fluidized bed is simultaneously present, the fluid phase of the fluidized bed is also present and exposed to X-rays. Reactants may vary over a wide range of liquids, gases, plasma, and in some cases, granular solids as well. The amounts of each reactant and the primary feedstock are metered using mass flow controllers as developed by the semiconductor industry. These controllers allow delivery of highly exacting amounts of materials with literally atomic levels of accuracy. This provides very precise control of the stoichiometry of the reactions.

The operation of the fluidized bed can be enhanced by one of several means in the UCP. First is by initiation of a plasma within the fluidized bed. This can be accomplished by one of several means. One is to turn on the x-ray emitter of the RXCP. This provides high energy radiation to ionize and enhance the reaction characteristics. A second way is to apply a high voltage DC signal to the insulated electrodes (which can also function as a heater or drier). This produces a lower energy plasma than is generated using X-rays. A third way is to apply an RF signal, again either through the insulated electrodes. This produces a plasma with energy between that produced by X-ray and that produced by DC. The choice of ionization means would be dependent on the desired end result from the resultant reaction. In this regard, it is noted that high temperature of the plasma generated in the reaction chamber can be sufficient to cause various reactions by a roasting process as well.

Due to the highly reactive nature of the plasmas contemplated by the current invention, it is desirable to provide a means to keep the plasmas away from the walls and injectors. There are three principle means to accomplish this: (1) electrostatically, which is the preferred embodiment (shown in FIG. 6); (2) electromagnetically (shown in FIG. 7): which is usable in some circumstances; and (3) using a physical isolation barrier (not shown). Starting with the latter, a physical isolation barrier involves placing a dielectric non-reactive insert into the reaction zone that contains the plasma to a specific region while still allowing the injection of various reactants and also illumination by both X-rays and secondary electrons.

FIG. 6 is a simplified cross-sectional view of an embodiment of a UCP that employs electrostatic plasma confinement, often referred to as field confinement or field enhancement, and is the preferred embodiment. In the embodiment shown, three equidistant electrodes 602, 604, 606 are positioned within the working zone of the main chamber insider of the inner wall 610 of the RXCP, but just outside of the reaction zone. The electrodes 602, 604, 606 are configured to produce a uniform, generally cylindrical or spherical field within which the plasma reactions will occur, referred to as a plasma confinement region 615. It is noted that other field configurations are possible. It is further noted that it is possible to utilize one or more of the reactant injectors as electrodes for the electrostatic field generation.

FIG. 7 is a simplified cross-sectional view of an embodiment of a UCP that employs electromagnetic plasma confinement. In the embodiment shown, four electromagnet coils 702, 704, 706, 708 are positioned around a reaction zone. The activation voltage/current can be either direct (DC) or alternating (AC). When activated the electromagnet coils 702, 704, 706, 708 generate the magnetic field illustrated by field lines 712. The magnetic field confines plasma generated within reaction zone by deflecting charged particles moving out of the confinement area (i.e., a current) back to the containment zone 715. It is noted that other coil and electromagnetic field configurations are possible.

Figure 11:
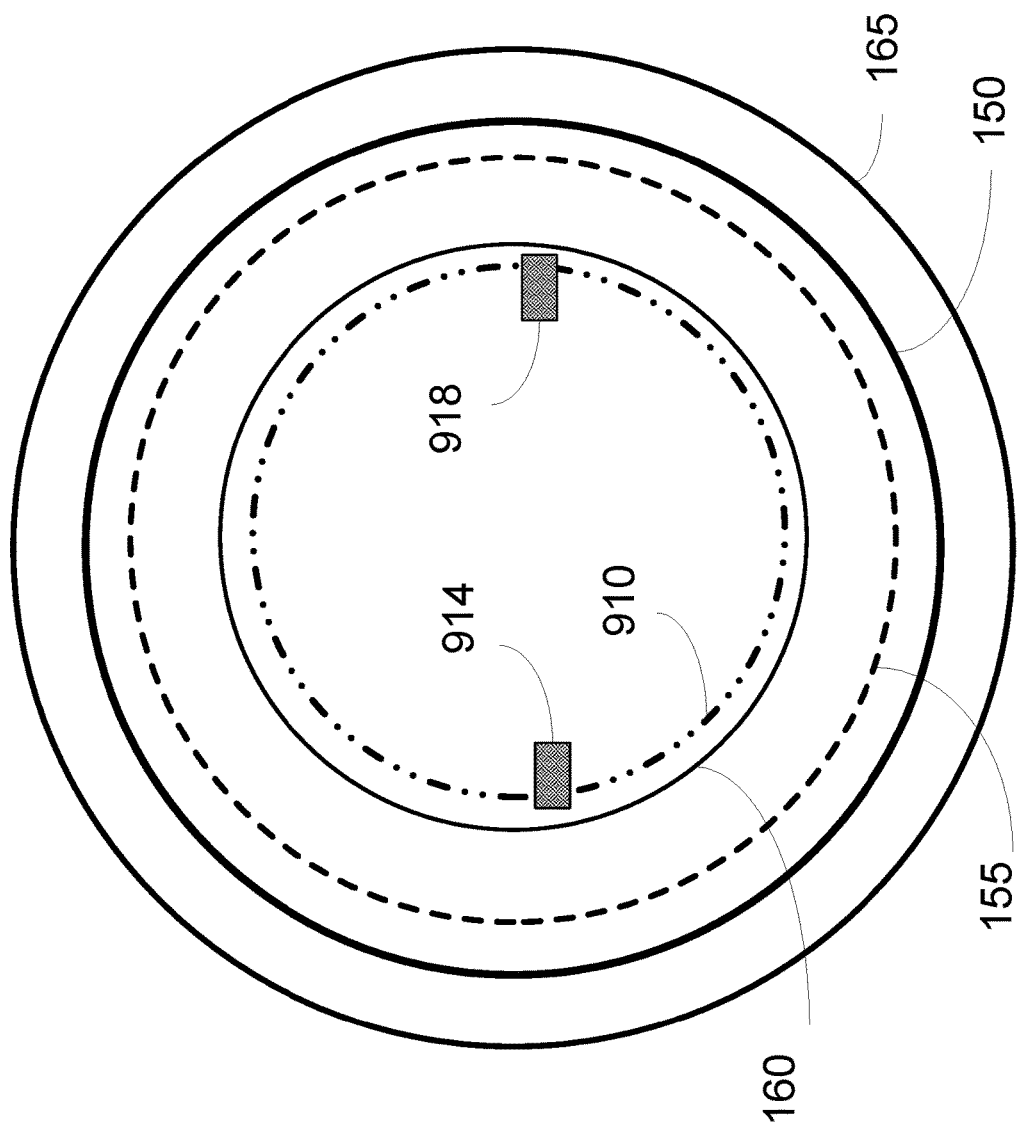
FIG. 11 is a schematic cross-sectional view of a UCP according an embodiment of the present disclosure having a heating/electrode element.

It is also desirable to be able to dry materials within the UCP. FIG. 11 is a cross-sectional view of an embodiment of a UCP having a drier element. In the axial cross-sectional view shown there are several concentric cylindrical elements, listed in turn from outermost from innermost: shielded housing 165; cathode 150, grid 155; anode 160 and drier element 910. The drier element can comprise a generally cylindrical serpentine resistance heating element which is mounted on electrical insulators 914, 918 just inside the inner wall of the hollow anode 160. The drier element 910 can also be used as an electrode for plasma initiation and maintenance by coupling the drier element to a switching means external to the inner volume of the UCP.

An online analysis of the feedstock through the mass spectrometer inlet port 118 is performed prior to processing. Following passage through the reactor, a second online chemical analysis is obtained by sampling the effluent at a second mass spectrometer inlet 180 at the upper end of the chamber to ensure that the reactants have been reacted to the desired state. It is noted that additional reactants can be added in the correct ratios in order to achieve a desired reactions and concentrations. Mass flowmeters (not shown in FIG. 1) provide an instrumented dispensing and feedback system for controlling the exact amounts of reactants supplied to the system. By controlling these factors, along with the X-ray voltage and current, it is possible to tune the system to produce a wide range of chemical outputs. A host computer (also not shown), equipped with suitable processing, memory and communication resources is coupled to the supply inlets, flowmeters and mass spectrometer and combines all information sources and utilizes artificial intelligence-based operations to ensure that reactor parameters are always optimized for the desired output product. The operation of the mass flow controllers is controlled by the host computer with inputs from residual gas analyzers and other analytic instruments attached to the system that monitoring the input and output of the system.

The host computer is configured to compare the mass spectrometer data generated from feedstock input and output, among other data sources, and compare the output data to a reference spectrum of a desired end product. Based on this analysis, the host computer determines whether to increase, decrease, or maintain the same flow rate of reactants. Once these adjustments are made, the host computer iterates additional analyses to determine if the adjustments made bring the end product closer to or further away from the desired end result product. Further adjustments can be made based on these iterations. The host computer continues the iterations until the output has stabilized within set lower and upper bounds. If the resulting output product is determined to be too far out of specification for the host computer to correct, then it shuts the chemical processes down and issues a notification to an operator. The host computer also monitors other critical functions for safety purposes and will shut down the system if any of the monitored parameters are out of specified range and thus presenting a safety hazard.

As reactions occur in the main chamber 135, certain compounds precipitate out and are removed from the output of the system through one of the output ports. After one or more iterations of this process, the effluent becomes free of unwanted chemical components and any biological components. For example, when the UCP is used for treatment of water, it decomposes any pharmaceutical or other complex organic compounds such as pesticides that are present.

The RXCP section of the UCP can be operated as a Flash X-ray irradiator (FXI). In FXI mode, high-intensity x-radiation is applied to the reaction zone typically with reactant feeds switched off. In this mode, feedstock is generally input through the feedstock input port with the remaining ports switched off. However, in some circumstances, the other inlet ports can be used to supply materials in the FXI mode. Depending on the materials present in the reaction (radiation) zone, decomposition, and cross-linking are typical of reactions that can occur in this mode. In this context, decomposition refers to what happens to complex molecules when subjected to intense X-ray irradiation, in which the X-rays are substantially in excess of the K-edge binding energies of the individual elements involved. This particular process is useful when organic components are present and it is desired to have them removed. The intense X-ray irradiation in FXI mode destroys any organic material. and decomposes it to its constituent elements which then recombine to their lowest energy state forms. Additionally, it is well known that ionizing radiation (X-rays) are capable of initiating cross-linking reactions in polymers and the like. By setting the correct operating parameters, the FXI easily achieves this operating environment. A detailed description of these processes and others is found in commonly-owned and assigned U.S. Pat. No. 8,019,047. For ease of reference, in this application the component used to generate X-rays in either the RXCP mode or the FXI is referred to as the RXCP.

To combine the fluidized bed and RXCP, certain modifications are made to take advantage of the fact that the RXCP typically incorporates a cylindrical process section. One possible modification is to add a perforated bottom plate with a feed connection for the fluidizing means, and inlet and outlet ports in the sides of the reaction area if the UCP is mounted vertically, or a perforated bottom plate if horizontal. Depending on the specification composition of the material to be separated, it may be desirable to incorporate a screening step either before or after the fluidized bed step, and external to the UCP, to increase the efficiency of separation. It is noted that the location of the inlet and outlet ports is dependent on whether the UCP is to be used in a batch or continuous mode, and whether it is to be used horizontally or vertically. When the UCP is operated as a fluidized bed in the horizontal position, it is necessary to relocate the diffuser and catalysts to accommodate this orientation, as the diffuser needs to be at the bottom of the fluidized bed in order for the bed to operate. The FXI functionality is achieved by turning off the reactant injection means and just operating the X-ray generating section of the UCP (i.e., the cathode, grid and anode). For the purposes of this application the batch processing vertical mode is a preferred embodiment but horizontal operation in the continuous mode is practical and can be employed in industrial scale processes.

Regardless of which mode the UCP it is used in, there are certain commonalities that are identified including the ability to operate in multiple sequential modes, including but not limited to: i) Fluidized Bed (FB) only; ii) RXCP only; iii) Flash X-ray only, full UC, which includes either iv) FB+RXCP; v) FB+RXCP+FXI; vi) FB+drying; vii) FB+RXCP+drying; viii) FB+RXCP+Field Enhancement; ix) RXCP+drying and x) RXCP+Field Enhancement. All of the above operating modes can be performed in either continuous or batch mode. All of the above modes can be performed with electromagnetic field enhancement, electrostatic field enhancement both enhancement techniques, and any of the above can be performed in plasma or non-plasma environments as required. It is again noted that the UCP mode includes the FXI capability by just switching off the reactants. Other FXI operations will also occur during this mode. The various combinations of process attainable will be apparent to a person of ordinary skill in the art.

Catalysts can be introduced into the UCP via the reactant feed to accelerate chemical reactions, or they can be permanently mounted in the reaction zone. Catalysts are not consumed in the catalyzed reaction hence they are unchanged after the reaction. In many types of reactions, often only very small amounts of catalyst are required. Furthermore, some reactions can only occur in the presence of a catalyst. Operations of the fluidized bed and RXCP (and FXI) can both be enhanced by the use of catalysts in certain situations. In general, chemical reactions occur faster in the presence of a catalyst because the catalyst provides an alternative reaction pathway or mechanism with a lower activation energy than the non-catalyzed mechanism. In catalyzed mechanisms, the catalyst usually reacts to form an intermediate, which then regenerates the original catalyst in the process. Many materials can function as catalysts, ranging from inorganic compounds such as Titania (Titanium Dioxide ($TiO_2$)) or Manganese Dioxide($MnO_2$) to complex organic compounds such as Wilkinson's catalyst, $RhCl(PPh_3)_3$. As an illustrative example, Wilkinson's catalyst loses one triphenylphosphine ligand before entering the true catalytic cycle. In general, ligands are viewed as electron donors and the metals as electron acceptors, (i.e., respectively, Lewis bases and Lewis acids). In plasma chemistry, the use of ligands may be obviated due to the surplus electrons that can be generated. This does not apply to all reactions but can be a major cost saving factor in some.

In the case of the Fluidized bed portion of the UCP, the use of catalysts has been studied, and numerous reactive processes conducted in Fluidized Beds are enabled by the presence of a catalyst. In the case of the RXCP section of the UCP, the introduction of a catalyst can be a pivotal addition in enabling a reaction. The operating principle of the RXCP (and the FXI) is that following the ionization step in these processes, the ions present will seek to immediately recombine into their lowest energy state as described above. By the introduction of a catalyst, this process can be altered to favor the formation of one compound over another.

To achieve improved process results for some uses of the UCP, it is frequently useful to perform pre-reaction filtration of the feedstock and reactant materials to remove as much particulate reactant matter as possible to minimize the amounts of material the reactor has to process, and post-filtration to remove precipitated material. This can be done by any of a number of well-known processes including, but not limited to, fluidized bed separation according to the present disclosure, screening, hydrocyclonic separation, centrifugal separation, basket type filters, or any of several others. The hydrocyclonic method is appropriate as it is a continuous high-volume method of separation, there are a number of suppliers of hardware, the hydrocyclonic separator requires less maintenance than basket type filters. A significant shortcoming of hydrocyclonic separation is that it is not as effective at removing fine and microscopic contaminants as basket type filters or other processes. We note that removal of as much material before the RXCP section of the UCP process reduces the amount of energy required to run the process.

Similarly, as the RXCP section of the UCP is designed to produce precipitates of several compounds in its output stream, these can be separated to render them usable for other purposes. Multi-stage basket filters of progressively finer pore sizes are a good way to achieve the desired state of cleanliness, although many other means are possible.

FIG. 5 is a schematic diagram showing an embodiment of a system including the UCP and a control system according to the present disclosure. In the system 500, a number of controlled inputs are fed to the UCP, and both inputs and outputs are monitored and under the control of a host computer 550. A feedstock supply 502, such as a tank or other container, delivers feedstock material through a supply line that is monitored by a feedstock flowmeter 504 which measures a mass flow rate of the input feedstock material through the feedstock supply line. Output from the feedstock flowmeter is delivered to the host computer 550 (through a wired or wireless connection). A feedstock supply control valve 508 is positioned on the feedstock supply line between the flowmeter 504 and the feedstock input port 110 of UCP 100. The feedstock control valve is also communicatively coupled to the host computer to receive control signals to open, close or modulate the valve depending on the operation of the UCP as determined by algorithms executed by the host computer 550.

Similarly, a fluidizing medium supply 512 delivers fluidizing medium through a supply line that is monitored by a fluidizing medium flowmeter 514 which measures a mass flow rate of the fluidizing medium through the fluidizing medium supply line. The fluidizing medium supply can comprise a pressurized liquid and/or gas tank. A fluidizing medium control valve 518 is positioned between the fluidizing medium flowmeter 514 and fluidizing medium input port 112 of the UCP 100. Both the fluidizing medium flowmeter 514 and the fluidizing medium control valve 518 are communicatively coupled to the host computer 550, the fluidizing medium flowmeter 514 providing measurement signals to the host computer 550 and the reactant supply control valve 528 receiving command signal from the host computer to regulate the reactant supply depending upon operating conditions of the UCP. Likewise, a reactant supply 522, which can also comprise a tank or other container, delivers reactant material through a supply line that is monitored by a reactant flowmeter 524 which measures a mass flow rate of the input reactant material. A reactant supply control valve 528 is positioned between the reactant flowmeter 524 and reactant input port 114 of the UCP 100. Both the reactant flowmeter 524 and the reactant supply control valve 528 are communicatively coupled to the host computer 550, the reactant flowmeter 524 providing signals indicative of the reactant mass flow rate to the host computer 550 and the reactant supply control valve 528 receiving command signal from the host computer to regulate the reactant supply depending upon operating conditions of the UCP. In some implementations, an additional reactant supply 532 delivers further reactants (which can be different from the reactants from reactant supply 522) into a secondary reactant supply line that leads into the feedstock supply line via the feedstock control valve 504. The feedstock and secondary reactant are thus supplied into the UCP 100 through the feedstock input line 110. A secondary reactant flowmeter 534 measures the mass flow rate through the secondary reactant supply line and delivers measurement signals to the host computer 550. The feedstock, fluidizing medium and reactant supplies 502, 512, 522, 532 can comprise pipes rather tanks in continuous mode.

The pairs of flowmeters and control valves, 504/508, 514/518 and 524/528 can be, but need not necessarily be, implemented in distinct devices. In some embodiments, both metering and fluid regulation functions can be performed by a single device using semiconductor technology as known in the art. The UCP also includes a recirculation loop for the fluidizing medium (not shown in FIG. 5) through which a pump recirculates fluid from the top of the main chamber of the reactor/concentrator back to the bottom.

The UCP 100 includes a first analytic output 118 that feeds a sample of input materials feed into the proximal end of the UCP 100 to a first mass spectrometer (not shown in FIG. 2). The output from the first mass spectrometer is fed to the host computer 250. At the distal end of the UCP there is a second analytic output 180 that feeds a sample of output products to a second mass spectrometer (also not shown). The output from the second mass spectrometer is also fed to the host computer 550. The distal end of the UCP also includes a main output port 145 for the products of reactions and other processes that occur within the UCP as well as a pressure relief vent 138. An output flowmeter 540 measures a flow rate of the output products and delivers measurement signals to the host computer 550. The material that exits through the main output port 145, which can be the desired product of reactions that are induced by RXCP or FXI operation, can lead to a tank, pipe, or additional process components. When used in batch mode, a single reactor can be used and the various process steps are implemented sequentially by changing various feeds and electrical parameters. When operated in continuous mode, fewer simultaneous operations are used and multiple UCP can be coupled sequentially or otherwise to implement a specific process.

The host computer 550 is also communicatively coupled to pressure relief 138 so as to regulate pressure within the UCP. The host computer 550 is configured to assess the flow rate information received from the flow meters as well as the information received from the mass spectrometers as to the composition of the input reactants (all reactants including the feedstock) and the output products, to regulate the flow of materials into the UCP via the control valves 504, 514, 524. For example, the host computer can determine that reactions are proceeding too quickly and execute commands to restrict the flow of input materials to slow down the reaction rate.

An electrical power supply 545 provides power to the cathode and grid of the UCP 100. The host computer 550 also provides control signals to operate the various components of the RXCP section of the UCP 100 and receives electrical signals for monitoring the state of the UCP. For example, the host computer 550 controls operation of the grid 155 of the RXCP to cause switch the electron gun on or off.

When the UCP is used for separation of feedstock materials, typically but not necessarily in fluidized bed operation, relatively heavier components exit from the lower output port 140 and lighter components exit from the upper output 142 (not shown in FIG. 2). Flowmeters (also not shown) can also be positioned at the lower and upper separation output ports 140, 142 to provide mass flow rate data for the separated flows to the host computer 550. As a result of the independent nature of the control system any feature or combination of features is possible with the UCP with the exception of the FXI and RXCP functions which are mutually exclusive.

The UCP described herein provides a number of synergies and advantages over the standalone components and other types of chemical processors. The increased mixing and contacting of reactants, catalysts, and feedstock due to the presence of the enhanced fluidized bed results in higher throughput and more complete reactions per stage than conventional individual reactors and processors. This is due to the fact that the UCP has increased versatility in that a single system is able to implement multiple processes. Additionally, the processes can be changed (e.g., changing operation from fluidized bed mode alone to fluidized by RXCP mode) without extensive changeover work. Put another way, the ability to support multiple operating modes in a single device means a single factory can produce multiple products or change process parameters and configurations more readily than with individual stages.

The UCP also has a more compact design and smaller footprint than conventional reactors of similar capabilities. The compact design enables a simpler electrical system with better coordination. The aforementioned advantages lead to lower manufacturing costs due to a more universal design requiring fewer variations, and greater economies of scale can be achieved. The UCP concept as presented herein represents an unanticipated means of achieving process flexibility heretofore unavailable in traditional chemical processing plants.

With respect to mining industry, and Rare Earth mining and recovery in particular, the UCP of the present disclosure fulfills a long-sought need. The types of operations the UCP can perform eliminate the need for toxic and contamination wet chemical processes that have been in use for hundreds of years. The impact on both the environment and civilian populations located proximate to these mining operations is immediate and enormous. Due to the combination of effective materials separation using the fluidized bed, elimination of environmental toxins, and abatement using the capabilities of the RXCP to modify or decompose dangerous byproducts, Rare Earth processing need no longer be an activity that is environmentally hazardous due to the creation of large quantities of toxic liquid waste and can be performed cost-effectively in locations and jurisdiction which would previously have been infeasible. For the United States, this represents a boon to national security, because the UCP can break the near monopoly that a small group of countries maintain in Rare Earth processing.

It is noted that other mining industries can benefit from the technology of the current invention. As an example, the oil and gas production industries produce vast quantities of waste byproducts that are radioactive and as such, present a serious environmental problem. Essentially the same process described herein for the removal of radioactive materials from phosphogypsum waste (see Example 2 below) can be utilized advantageously by the oil and gas industry for essentially the same requirement (i.e. removal of radioactive material from a process stream (see Example 3 below). As is the gas with phosphogypsum, Radium and Radon are two of the major radioactive components that must be remediated.

Sample Reactions: To illustrate examples of UCP operation, several sample reactions are presented:

1. Manufacture of Hydrogen Peroxide: To manufacture Hydrogen Peroxide ($H_2O_2$) in the UCP, purified water is used as the primary feedstock. In the RXCP mode, it is ionized and reacted with purified oxygen to produce $H_2O_2$ in the following reaction:

$$2H_2O + O_2 \rightarrow 2H_2O_2 \quad (2)$$

{in the presence of X-rays}

This reaction can be adjusted to produce any concentration of $H_2O_2$ desired. It is noted that at concentrations above 20%, the $H_2O_2$ becomes increasingly unstable to a point where it can explode. For most concentrations above 10%, a stabilizer chemical is added to mitigate this problem.

Traditional methods of production of $H_2O_2$ involve the use of large quantities of Ammonia, Sulfuric Acid, 2-ethylanthraquinone, ammonium persulfate, and others, all of which are toxic and considered environmental pollutants. The UCP/RXCP process eliminates all these materials and the downstream pollutants they produce. It requires just water, oxygen and electricity to make $H_2O_2$. If desired, and the energy is available, the incoming waste stream can be electrolyzed to produce the required amounts of oxygen with only hydrogen as a byproduct.

2. Manufacture of Phosphoric Acid, and Hydrofluoric Acid from Fluorapatite Ore: The traditional wet chemistry process for achieving this is:

$$Ca_5F(PO_4)_3 + 5H_2SO_4 + 10H_2O \rightarrow 3H_3PO_4 + 5CaSO_4 \cdot 2H_2O + HF. \quad (3)$$

From this formula, we see that Ca5F(PO4)3 (Fluorapatite) is reacted with Sulfuric Acid (H2SO4) and water to produce Phosphoric Acid, Hydrofluoric Acid, and Phosphogypsum. Phosphogypsum ((CaSO4.2H2O) is the byproduct of this process and is a hydrate of Calcium Sulphate). The end products of this reaction are then subjected to further separation steps to isolate the individual compounds. To achieve the same end products using a plasma-based process, Ca5F(PO4)3 is mixed with water and allowed to flow through an RXCP or UCP reactor. There, it is ionized and reacted with Hydrogen Sulfide gas and Oxygen to produce the same end products. Care must be taken in setting the reactor operating parameters to maintain the stoichiometry of the process. The reaction becomes: To achieve the same end products in the UCP, $Ca_5F(PO_4)_3$ is mixed with water and allowed to flow through the UCP reactor. There, it is ionized and reacted with Hydrogen Sulfide gas to produce the same end products. Care must be taken in setting the UCP reactor operating parameters to maintain the stoichiometry of the process. The reaction becomes:

$$Ca_5F(PO_4)_3 + 5H_2S + 10H_2O + 10O_2 \rightarrow 3H_3PO_4 + 5CaSO_4 \cdot 2H_2O + HF \quad (4)$$

Note that instead of $H_2SO_4$ being used as a liquid reactant (traditional process), the plasma process uses Hydrogen Sulfide and Oxygen as gaseous reactants which are better suited to the plasma process. In the preferred embodiment, with the correct choice of operating conditions, it is possible to get the Phosphoric acid to come off as a liquid, the Phosphogypsum to come off as a solid (precipitate), and the HF to come off as a gas. This eliminates the need for further process steps. The advantage that the UCP brings to this process is that there are no toxic liquid wastes as any unwanted byproducts are given off as gases and can be destroyed by pyrolysis unit pollution control equipment on the exhaust of the process pumps. This is an incinerator placed in series with the exhaust of the process pumps and the building exhaust to the atmosphere. The use of plasma technology is standard in modern semiconductor processing. It is noted that there are other plasma based approaches to achieve the same end products.

3. Separation of Actinides from Fluorapatite or Phosphogypsum:

Fluorapatite rarely occurs by itself. It is normally found in combination with Hydroxyapatite [Ca5(PO4)3OH], a variety of rare earths (Lanthanides) and radioactive minerals (Actinides), typically Uranium, Radium, and Thorium. Other Actinides are frequently found in smaller quantities as well. It is thus necessary, at some point, to separate the Actinides from the Fluorapatite (or Phosphogypsum) and Lanthanides. Depending on local conditions and regulations at the mining site, this separation can be done either before or after the Fluorapatite reaction described in #2 (above), but usually it is done before so as to not create a large volume of radioactive waste. It is desirable to remove any radioactive materials (Actinides) from Fluorapatite or Phosphogypsum (a byproduct of fertilizer, hydrofluoric Acid, and Phosphoric Acid manufacturing) so that these products and the residual Phosphogypsum can be safely used for other purposes. The existing wet chemical processes produce large amounts of toxic pollutants. In some cases, the use of the UCP eliminates wet chemistry entirely and its associated pollutants when the Actinides are not chemically bound to the phosphogypsum. In this case, the UCP is used in fluidized bed mode. The Fluorapatite or Phosphogypsum (feedstock, in this specific case) is introduced as a dry powder and fluidized with (typically) air. This causes portions of the feedstock to rise to the top of the column and the Actinides to fall to the bottom of the column where they exit the column from the respective outlet ports 140 for the Phosphogypsum and 142 for the Actinides. When the UCP is used in this mode, the separation is accomplished on the basis of the density of the particles. In cases where the compounds are chemically bound, it is appropriate to use a reactive plasma step before the physical separation step to achieve complete separation of the radioactive materials from the feedstock.

There are other means of separating Actinides and Lanthanides from Phosphogypsum or Fluorapatite using the UCP. Typically, Uranium, Thorium and Radium are the primary Actinides found in Fluorapatite and therefore Phosphogypsum. One such means involves reacting the Actinide (as a Hydrate) with either water and NO (Nitric Oxide, as a gas), or HCL (as a gas) to produce:

$$ACT(OH)_3 + 3HNO_3 \rightarrow ACT(NO_3)_3 + 3H_2O \tag{5}$$

$$ACT(OH)_3 + 3HCl \rightarrow ACTCl_3 + 3H_2O \tag{6}$$

where ACT stands for the specific Actinide compound. Alternatively, Uranium or Thorium may be separated out using ammonia and carbon dioxide gases with ammonium hydroxide (aqueous ammonia) as a commercially saleable byproduct.

$$UO_2(OH)_2 + 3(NH_4)_2CO_3 \rightarrow (NH_4)_4[UO_2(CO_3)_3] + 2NH_4OH \tag{7}$$

The specific reaction chosen is dependent on the available raw materials, which may be used as is or with some degree of preprocessing to adjust both the mechanical and electrical properties of these materials.

4. Removal of pharmaceuticals and other organic and biologic contaminants: A major pollution problem facing most countries is the presence of pharmaceuticals and other organic chemical contaminants in water. In this process, water which has, for example, pharmaceutical products contaminating it, (or other organic contaminants), the UCP is run in the FXI mode. Here the contaminated water is exposed to a high dose of X-radiation. This has the effect of both ionizing the water while simultaneously breaking all the bonds of the organic contaminants (including the pharmaceuticals). All the resulting ions then recombine to their lowest energy states in accordance with the process as previously defined in U.S. Pat. No. 8,019,047 "Flash X-ray Irradiator". The Hydrogen and Oxygen ions also recombine to go back to water. The resulting water is now free from long chain organic contamination and sterilized as well. The reason that the UCP system (in the FXI or RXCP modes) is able to achieve this level of ionization and the associated decomposition is that the incident energy from both the X-rays and the secondary electrons generated is many times that K-shell energy level, the energy level at which the K-shell electrons (and all others) are knocked off the atom. This applies to all organic compounds, biologicals, petrochemicals, and pharmaceuticals. It is noted that the UCP can be run in the RXCP mode and used to add Hydrogen Peroxide ($H_2O_2$) as previously described to the contaminated water to further remediate the pollution.

X-Radiation, in sufficient quantity, is lethal to biological organisms by several means, including but not limited to, disruption of DNA by breaking of molecular bonds, inducing genetic damage, and chemical changes in key biological macromolecules, any of which can lead to the death of the organism. During sterilization treatment, the sample of interest is bombarded with high energy X-rays, electrons, or gamma rays at sufficient fluence, which leads to the formation of extremely unstable free radicals, molecular ions and secondary electrons, as well as X-rays. These radiation products then react with nearby molecules to fracture and alter chemical bonds. DNA in particular is highly sensitive to the damaging effects of radiation and will break, depolymerize, mutate and alter structure upon exposure to ionizing radiation. Incomplete repair of DNA damage ultimately leads to loss of genetic information and cell death. The sensitivity of a given biological organism to radiation is given by the decimal reduction dose ($D_{10}$ value), the dose of radiation which leads to a 10-fold reduction in microorganism population.

5. Elimination of Marine Contaminants such as Oil and Chemical Spills, Bacterial and Algae Overgrowths: In this application, the system is mounted on a boat, hovercraft or other type of marine vehicle, preferably a catamaran and there is a large scoop positioned between the bows that can be lowered into the water while the boat is moving. The scoop directs the contaminated water up through a pipe into the UCP being operated in either the FXI mode (simplest form) or the RXCP mode where oxygen is added to form hydrogen peroxide. In the FXI mode, just radiation is used to decompose any organics, and kill any bacterial or other algae that may be present. In the RXCP mode, both radiation and oxidation are used to remediate and eliminate the contaminant. It is noted that any fish that pass through the reactor will likely be killed in either process mode. This can be precluded by using a mesh over the inlet to block fish from entering the unit. It is noted that this implementation may require periodic cleaning to remove fish and other materials caught by the mesh or by sending signals into the water, directed ahead of the advanced vessel to drive the fish away. It is further noted that Oxygen is not the only additive that can be used in this application. Other gases, such as Chlorine, can successfully be used to achieve the same ends.

To implement this application, in addition to the UCP or derivatives, a generator and high voltage power supply would have to be mounted on the boat. Further, if the boat speed is not above some predefined limit, it will be necessary to include a pump to ensure that enough water passes through the UCP or derivatives. Once through the Irradiation device, the processed water is dumped off the stern back into the body of water from which it was drawn. It is noted that this method of removal of algal growths is not limited to that which float on the surface. The scoop can be deployed at any desired depth, with due consideration given to the speed of the vessel through the water and appropriate caution to prevent entanglement with underwater obstacles. On-board sonar can be used to prevent entanglement of the scoop with underwater obstacles.

Similarly, in the case of oil and chemical spills, the same apparatus is used. Care must be taken to protect the operators of the vessel if there are toxic fumes or flammable materials involved.

In the case of very large spills, typically in an ocean, gulf, large bay or sound, etc. a faster craft may be required. This also increases the power demand as the irradiation system must be run at higher irradiation levels. In this case, a small jet engine (typically the size used for a large business jet) coupled to a generator, such as is used by the electric power industry for peak power generation can be used. The exhaust generates thrust to move the boat at high speeds, and the generator can produce power into the MegaWatt range. This type of motor generator is commercially available from several suppliers. A smaller conventional motor and propeller system is also included for low-speed maneuvering. It is essential that the maneuvering system propeller be able to be feathered to allow for high-speed operation.

It is necessary to provide radiation protection for the operators of the irradiation vessel. This can be in the form of lead or other high atomic number shield materials placed so as to block radiation from the irradiation system from hitting the operator. It is noted that when the system is not operating there is no radiation hazard to the operator and crew. Alternatively, the marine vehicle can be remotely operated to put the operators at a safe distance from the radiation produced by the UCP.

It is noted that other implementations of the irradiation system being integrated onto a boat are possible and practical.

It is to be understood that any structural and functional details disclosed herein are not to be interpreted as limiting the systems and methods, but rather are provided as a representative embodiment or arrangement for teaching one skilled in the art one or more ways to implement the methods.

It is to be further understood that like numerals in the drawings represent like elements through the several figures, and that not all components or steps described and illustrated with reference to the figures are required for all embodiments or arrangements.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the either of the terms "comprises" or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. A universal chemical processor (UCP) including a reactor vessel having a central longitudinal axis and main chamber, the UCP comprising:
    a first inlet port for a main feedstock leading to the main chamber;
    a second inlet port for a fluidizing medium leading to the main chamber;
    a third inlet port for one or more reactants leading to the main reactor chamber; and
    a reactive X-ray chemical processor (RXCP) including:
        a cold cathode extending along the longitudinal axis in the main chamber;
        a grid positioned concentrically and more centrally with respect to the cathode in the main chamber; and
        an anode positioned concentrically and more centrally with respect to both the cathode and grid;
    wherein, in operation, a fluidized bed can be supported in the main chamber when a fluidizing medium and feedstock are supplied to the main chamber through the first and second inlet ports; and
    wherein, when switched on, the cathode of the RXCP emits electrons onto the anode, which upon impact of the electrons emits X-rays into a radiation zone within the main chamber of the vessel, the X-rays being capable of ionizing feedstock and reactants, inducing chemical reactions, and sterilizing and decomposing any organic materials within the radiation zone.

2. The UCP of claim 1, further comprising catalyst material positioned within the main chamber.

3. The UCP of claim 2, wherein the catalyst material is installed within one of screens, plates, and containers within the main chamber.

4. The UCP of claim 1, wherein, in operation, the fluidized bed can be supported while the RXCP is switched on.

5. The UCP of claim 1, wherein, in operation, the fluidized bed can be supported while the RXCP is switched off.

6. The UCP of claim 1, wherein, in operation, the RXCP can function in flash X-ray irradiation (FXI) mode when a feed of reactants other than the main feedstock through the first inlet port is switched off.

7. The UCP of claim 1, wherein the first, second and third inlet ports are shielded against X-ray radiation.

8. The UCP of claim 1, wherein the first feedstock inlet port and second fluidizing medium port deliver feedstock and fluidizing medium, respectively, to a base of the reactor vessel upstream of the radiation zone.

9. The UCP of claim 8, further comprising a diffuser positioned in the base of the reactor downstream from the first feedstock inlet port and second fluidizing medium inlet port and operative to aid in distributing the fluidizing medium and feedstock uniformly into the main chamber.

10. The UCP of claim 8, further comprising a lower output port position at a first height in the main chamber and an upper output port positioned at a second height in the main chamber higher than the first height, wherein, during fluidized bed operation, chemical species separate according to density and heavier elements are output from the main chamber from the lower output port and lighter elements are output from the upper output port.

11. The UCP of claim 1, wherein the feedstock input port leads through a shielded injector conduit having an outlet that is centrally located within the main chamber.

12. The UCP of claim 7, wherein the third inlet port for one or more reactants leads to a shielded conduit having nozzles that open to release reactants directly in the main chamber.

13. The UCP of claim 1, further comprising at least one electrode positioned within the main chamber configured to induce or maintain a plasma within the main chamber.

14. The UCP of claim 10, further comprising a main outlet port for outputting products of chemical reactions that occur within the main chamber.

15. A marine vehicle adapted to treat marine contaminants at a contaminated site comprising:
    means for propelling the vehicle;
    an onboard generator;
    a high voltage power supply coupled to the onboard generator;
    a universal chemical processor (UCP) according to claim 1 coupled to the high voltage electrical power generator; and
    a scoop for gathering water at the contaminated site;
    wherein the scoop is coupled to the feedstock input of the UCP and the UCP is operated to decompose any organic components and to and kill any bacteria and algae present in the contaminated feedstock and non-contaminated output from the UCP is directed out of the vehicle and back into water at the contaminated site.

16. The marine vehicle of claim 15, wherein the means for propulsion comprises a jet engine that provides high speed propulsion.

17. The marine vehicle of claim 15, wherein the means for propulsion further includes a separate low speed engine that is adapted for maneuvering the marine vehicle at low speed.

18. The marine vehicle of claim 15, wherein the UCP is operated in FXI mode to decompose any organic components including oil compounds and related chemical wastes and to kill any bacteria and algae.

19. The marine vehicle of claim 15, wherein the UCP is operated in RXCP mode to decompose any organic components including oil compounds and related chemical wastes and to and kill any bacteria and algae.

20. The marine vehicle of claim 15, further comprising radiation shielding positioned around the UCP to protect personnel on the vehicle from irradiation during operation of the UCP in RXCP or FXI mode.

21. The UCP of claim 1, further comprising a drier positioned in the main chamber and adapted to remove water or other liquid content from reactants and products.

22. A universal chemical processor (UCP) including a reactor vessel having a central longitudinal axis and main chamber, the UCP comprising:
    a first inlet port for a main feedstock leading to the main chamber;
    a second inlet port for a fluidizing medium leading to the main chamber;
    a third inlet port for one or more reactants leading to the main reactor chamber; and
    a reactive chemical processor (RCP) including:
        a radiation source adapted to emit X-radiation into the main chamber;
    wherein, in operation, a fluidized bed can be supported in the main chamber when a fluidizing medium and feedstock are supplied to the main chamber through the first and second inlet ports; and
    wherein, when switched on, the radiation source of the RXCP emits X-radiation into a radiation zone within the main chamber of the vessel capable of ionizing feedstock and reactants, inducing chemical reactions, and sterilizing and decomposing any organic materials within the radiation zone.

23. The UCP of claim 22, wherein the radiation source includes a radioisotope.

* * * * *